(12) United States Patent
Nguyen et al.

(10) Patent No.: US 10,689,610 B2
(45) Date of Patent: Jun. 23, 2020

(54) GAS-FED FERMENTATION REACTORS, SYSTEMS AND PROCESSES UTILIZING GAS/LIQUID SEPARATION VESSELS

(71) Applicant: Calysta, Inc., Menlo Park, CA (US)

(72) Inventors: Luan Thanh Nguyen, San Ramon, CA (US); Joshua A. Silverman, Los Altos Hills, CA (US); Graham Ian Aylen, Knowbury (GB)

(73) Assignee: Calysta, Inc., Menlo Park, CA (US)

( * ) Notice: Subject to any disclaimer, the term of this patent is extended or adjusted under 35 U.S.C. 154(b) by 0 days.

(21) Appl. No.: 16/102,448

(22) Filed: Aug. 13, 2018

(65) Prior Publication Data

US 2019/0048308 A1    Feb. 14, 2019

Related U.S. Application Data

(60) Provisional application No. 62/545,347, filed on Aug. 14, 2017.

(51) Int. Cl.
| | |
|---|---|
| *C12M 1/00* | (2006.01) |
| *C12M 1/107* | (2006.01) |
| *B01D 19/00* | (2006.01) |
| *C12M 1/12* | (2006.01) |

(52) U.S. Cl.
CPC ............. *C12M 45/04* (2013.01); *B01D 19/00* (2013.01); *B01D 19/0042* (2013.01); *C12M 21/04* (2013.01); *C12M 21/12* (2013.01); *C12M 23/06* (2013.01); *C12M 29/18* (2013.01); *C12M 29/20* (2013.01)

(58) Field of Classification Search
CPC ...... C12M 29/18; C12M 29/20; C12M 47/10; C12M 45/04; B01D 19/0042

USPC .............................. 210/194, 603; 435/293.1
See application file for complete search history.

(56) References Cited

U.S. PATENT DOCUMENTS

| | | |
|---|---|---|
| 4,530,762 A | 7/1985 | Love |
| 4,704,363 A | 11/1987 | Ziegler |
| 4,906,574 A | 3/1990 | Erdei et al. |
| 5,073,496 A | 12/1991 | Oosterhuis et al. |
| 6,492,135 B1 | 12/2002 | Larsen |
| 6,689,601 B2 | 2/2004 | Koffas et al. |
| 7,575,163 B2 | 8/2009 | Malik |
| 7,579,163 B2 | 8/2009 | Eriksen et al. |
| 8,354,063 B2 | 1/2013 | Hottovy et al. |

(Continued)

FOREIGN PATENT DOCUMENTS

| | | |
|---|---|---|
| EP | 0 185 407 B1 | 1/1990 |
| EP | 0 418 187 A1 | 3/1991 |

(Continued)

OTHER PUBLICATIONS

U.S. Appl. No. 15/625,858, filed Jun. 16, 2017, Gas-Fed Fermentation Reactors, Systems and Processes.

(Continued)

*Primary Examiner* — Claire A Norris
(74) *Attorney, Agent, or Firm* — Seed IP Law Group LLP

(57) ABSTRACT

Reactors, systems and processes for the production of biomass by culturing microorganisms in aqueous liquid culture medium circulating inner loop reactor which utilize nonvertical pressure reduction zones are described. Recovery and processing of the culture microorganisms to obtain products, such as proteins or hydrocarbons is described.

21 Claims, 9 Drawing Sheets

(56) References Cited

U.S. PATENT DOCUMENTS

| | | | |
|---|---|---|---|
| 8,648,209 | B1 | 2/2014 | Lastella |
| 9,114,357 | B2 | 8/2015 | Block et al. |
| 10,184,103 | B2 | 1/2019 | Larsen |
| 2004/0241790 | A1* | 12/2004 | Eriksen .............. A23J 1/005 435/41 |
| 2007/0003602 | A1 | 1/2007 | Johannessen et al. |
| 2011/0244543 | A1 | 10/2011 | Larsen |
| 2015/0259639 | A1 | 9/2015 | Silverman et al. |

FOREIGN PATENT DOCUMENTS

| | | |
|---|---|---|
| EP | 1 183 326 B1 | 3/2007 |
| EP | 2 789 396 A1 | 10/2014 |
| WO | 00/70014 A1 | 11/2000 |
| WO | 01/60974 A2 | 8/2001 |
| WO | 02/18617 A2 | 3/2002 |
| WO | 02/20728 A2 | 3/2002 |
| WO | 02/20733 A2 | 3/2002 |
| WO | 03/016460 A1 | 2/2003 |
| WO | 2010/056461 A2 | 5/2010 |
| WO | 2010/069313 A2 | 6/2010 |
| WO | 2014/058761 A1 | 4/2014 |
| WO | 2017/218978 A1 | 12/2017 |

OTHER PUBLICATIONS

Peterson et al., "Mixing and Mass Transfer in a Pilot Scale U-Loop Bioreactor," *Biotechnology and Bioengineering 114*(2):344-354, 2017.

U.S. Appl. No. 16/405,587, filed May 7, 2019, Gas-Fed Fermentation Reactors, Systems and Processes.

Spath et al., "Preliminary Screening—Technical and Economic Assessment of Synthesis Gas to Fuels and Chemicals with Emphasis on the Potential for Biomass-Derived Syngas," NREL/TP-510-34929, *National Renewable Energy Laboratory*, Golden, Co., Dec. 2003, 160 pages.

Sulter et al., "Proliferation and metabolic significance of peroxisomes in *Candida boidinii* during growth on D-alanine or oleic acid as the sole carbon source," *Arch Microbiol 153*:485-489, 1990.

Taweel et al., "Effect of Mixing on Microorganism Growth in Loop Bioreactors," *International Journal of Chemical Engineering 2012*: 2012, 12 pages.

Van Dien et al., "Reconstruction of C3 and C4 metabolism in *Methylobacterium extorquens* AM1 using transposon mutagenesis," *Microbiology 149*:601-609, 2003.

* cited by examiner

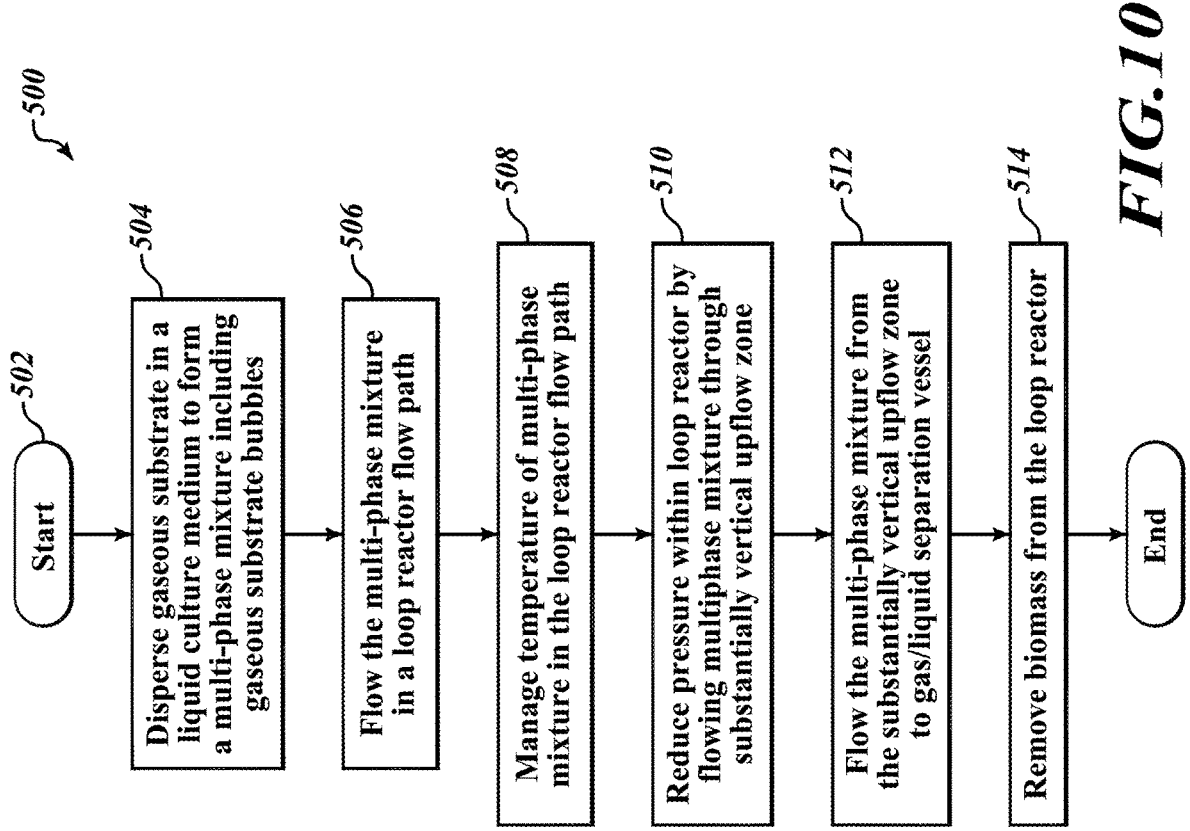

GAS-FED FERMENTATION REACTORS, SYSTEMS AND PROCESSES UTILIZING GAS/LIQUID SEPARATION VESSELS

BACKGROUND

Technical Field

This invention is related to gas fed fermentation reactors, systems and processes useful in fermentation that utilize gas/liquid separation vessels and, in particular, fermentation systems using a gaseous substrate.

Description of the Related Art

With the ever increasing depletion of fossil fuel deposits, the increasing production of greenhouse gases and recent concerns about climate change, substituting biofuels (e.g., ethanol, biodiesel) for fossil fuels has become an industrial focus. However, biofuels generated to date have their own difficulties and concerns. First generation biofuels are derived from plants (e.g., starch; cane sugar; and corn, rapeseed, soybean, palm, and other vegetable oils), but these fuel crops compete with crops grown for human and animal consumption. The amount of globally available farm land is insufficient to satisfy the increasing needs for both food and fuel. To reduce the demand placed upon food producers for biofuel compatible grains, second generation biofuels using alternative biological material such as cellulose or algae are under development. However, technical difficulties in production, along with the high cost of production, have not made second generation biofuels any more cost-effective or accessible.

Third or next generation biofuels are made using alternative, non-food based, carbon feedstocks. As part of this effort, the use of alternative, non-biological based, feedstocks, in the production of higher hydrocarbon compounds including fuels, lubricants, and plastics is gaining ever-increasing momentum. Such feedstocks may include one or more carbon-containing compounds or mixtures of carbon-containing and non-carbon-containing compounds that include, among others, methane and syngas. Methane, for example, is a relatively abundant, naturally occurring and found in many locations throughout the world. Methane is also produced during many biological decay processes, and thus may be captured from waste treatment and landfill facilities. For its relative abundance, methane is a potent greenhouse gas, having 23× the relative greenhouse gas contribution of $CO_2$. Historically, methane has been viewed as a somewhat valuable byproduct that is difficult to convert to higher value products or to transport to the marketplace from remote or stranded locations such as remote gas fields or off-shore production platforms. Methane from such sources, as well as the methane produced by biological decomposition processes occurring at sewage treatment facilities and landfills, is primarily either vented or flared. The ability to economically and efficiently convert methane and similar carbon-containing gases to one or more higher value $C_2$ or higher hydrocarbons would permit producers to take advantage of a relatively abundant, non-biologically produced, feedstock while, at the same time, providing a significant environmental benefit.

The rise in domestic production of methane capability makes methane more readily available domestically. Domestic natural gas is primarily produced by hydraulic fracturing ("fracking"), but methane can also be obtained from other sources, such as landfills and sewage. But methane's volatility makes the transport and/or direct usage of methane as a fuel problematic.

For these reasons, a strong incentive exists to convert the methane to one or more liquid products, for example motor fuels, to permit easier transport to the point of use or sale. Two main approaches are currently being pursued: liquefaction leading to liquefied natural gas (LNG) and chemical conversion to convert gas-to-liquid (GTL) (Patel, 2005, 7th World Congress of Chemical Engineering, Glasgow, Scotland, UK). The Fischer Tropsch (F-T) process is currently the most prevalent approach for converting large quantities of methane to higher-order hydrocarbons (Patel, 2005). Note that the F-T process takes syngas as an input; syngas is produced from natural gas by steam reforming (syngas can also be sourced from coal gasification, by high temperature reaction with water and oxygen). The F-T process yields petroleum products consistent with today's fuel supply, but suffers from a number of drawbacks, including low yields, poor selectivity (making downstream utilization complex), and requires significant capital expenditure and scale to achieve economical production (Spath and Dayton, December 2003 NRELITP-510-34929). The massive scale required for an F-T plant (generally in excess of two billion dollars in capital cost [Patel, 2005]) also represents a significant limitation due to the large amount of methane feedstock required to offset the enormous capital cost of the F-T process. As methane transportation is prohibitively expensive in most cases, such a plant must be co-located with a steady, reliable, and cost efficient source of methane, usually in the form of a significant methane reservoir or a methane pipeline. An additional cost and scaling factor is the economics of gas-scrubbing technologies (Spath and Dayton, 2003), since F-T catalysts are quite sensitive to common contaminants found in natural gas that pass unaffected through the syngas conversion process.

The requirements for ready access to large volumes of a relatively clean methane-containing gas, combined with a massive capital investment, currently limit natural gas based F-T plants to successful and economically viable operation in only a few locations worldwide (Spath and Dayton, 2003). The high minimum processing requirement for a gas-to-liquids process or liquified natural gas plant, combined with the high cost of transport, result in smaller methane sources remaining as "stranded" gas deposits. Such stranded gas can include, but is not limited to, natural gas produced at off-shore oil wells, or methane off-gas from landfills. Due to the current absence of efficient small-scale conversion technologies, such stranded gas sources are typically vented to atmosphere or flared, as methane accumulation presents a significant safety risk. Gas-to-liquids facilities using the Fischer-Tropsch process have been in operation semi-continuously since 1938. Several companies are currently investigating introduction of new plants given the current availability and price of methane discussed above. However, despite significant research and development over the last 70+ years, the limitations of Fischer-Tropsch technology prevent broad adoption of commercial gas-to-liquids processes.

Advances in the efficiency in animal feed utilization have been achieved over the past several decades through the use of feed additives. These added substances augment the nutrient content, energy content, and/or disease fighting properties of animal feed compositions. A growing challenge for commercial animal producers is the rising cost of grain. The rising costs are due in part to competing demands for grains for biofuel and human food use. With the rising cost of grain and protein complements, coupled with limited land available for feed production, alternative low-cost animal feed products with beneficial nutritive and disease fighting properties are desirable.

A number of different protein-containing materials have been proposed as substitutes for more traditional sources of protein, such as fish meal, soya products and blood plasma, in human foods and as animal feed. These protein-containing materials include single cell microorganisms such as fungi, yeasts and bacteria which contain high proportions of proteins. These microorganisms may be grown on hydrocarbon or other substrates.

In view of the above, biological fermentation using $C_1$ substrates as a carbon source presents an attractive solution to both the current competition between food sources and fermentation for producing chemicals/fuels, the need for alternative low-cost animal feed products, as well as the lack of good options for utilization of natural gas. However, fermentation of gaseous substrates such as methane, CO, or $CO_2$ presents significant challenges due to the requirement that the carbon substrate must be transferred from the gas phase to an aqueous phase to allow for uptake and metabolism by the $C_1$ metabolizing non-photosynthetic microorganisms in culture. Simultaneously, other gasses such as $O_2$ or $H_2$ may also be required to be transferred from the gas phase to allow cellular metabolism to progress (aerobic or anaerobic metabolism, respectively). Waste products (such as $CO_2$ in the case of aerobic metabolism) must be isolated from the microorganisms to allow for efficient microbial growth. Further, the heat generation from metabolism of $C_1$ substrates is significant and the system requires cooling to maintain optimal conditions for microbial growth. In addition, biological fermentation of $C_1$ substrates, sometimes results in $C_1$ substrates, such as methane, being in the same vessel as an oxidizing agent, such as oxygen. Care must be taken to avoid combustion and deflagration.

Convective mass transfer from the liquid phase to the vapor phase can be described with a mass transfer coefficient. The flux is equal to the product of the mass transfer coefficient, the surface area, and the concentration difference (Flux=kAΔC).

The mass transfer coefficient is influenced by a variety of factors including the size of the molecule to be transferred, its solubility in the aqueous phase, and the size of the boundary layer between the phases (typically controlled in fermentation systems by mixing speed and turbulence). The surface area between the gas and liquid phases in most fermentation systems is primarily limited by the bubble size of the input gas. Bubble size can be controlled by introducing the gas through small pores, as well as increasing shear forces to break apart bubbles and prevent coalescence. The concentration difference can be the concentration difference across the gas phase boundary layer, the concentration difference across the liquid phase boundary layer, the concentration difference between the bulk vapor and the vapor which would be in equilibrium with the bulk liquid, or the concentration difference between the bulk liquid and the liquid which would be in equilibrium with the bulk vapor. In most fermentation systems, the concentration difference is controlled by the pressure of the gas phase.

Conventional fermentation systems (bioreactors) achieve gas mixing by one of two methods: stirring or airlift. Stirred fermentors achieve mixing by means of stirring blades generally placed centrally in a single large fermentor. The stirrer blades generate turbulence and shear in the liquid while gas bubbles are introduced at the bottom of the fermentor, thus impeding the progress of the bubbles as they travel up the fermentor and shearing the gas bubbles to reduce the tendency of the bubbles to coalesce within the fermentor. The advantage of this type of fermentor is the fast, relatively homogeneous mixing and gas bubble dispersion that is possible due to the high speed of the mixing blades. However, this type of fermentor can be difficult to scale-up, as the energy requirements to obtain the same rate of mixing and mass transport can be prohibitive as the volume increases. Further, the vigorous mixing implies a significant heating of the fermentation liquid, and the use of a single large fermentor limits the surface area available for heat exchange cooling.

Airlift fermentors avoid mechanical stirrers by incorporating a flow path for the liquid. Airlift fermentors have a downflow and an upflow section which are interconnected at both ends; these sections can either be separate units (referred to as a loop fermentor), or concentric (airlift fermentor). In either case, gasses are supplied at the bottom of the upflow section through a bubble-generating apparatus. The bubbles mix with the liquid, reducing the density of the liquid and causing the gas-liquid mixture to rise through the upflow section. The rising mixture displaces liquid at the top of the reactor, which travels down the downflow section to replace the liquid at the bottom, establishing a circular flow in the fermentor. In order to obtain a long residence time for the gas bubbles in the liquid, airlift fermentors are generally tall and have a limited transverse cross-sectional area. This implies that the gas must be supplied at a relatively high pressure to overcome hydrostatic pressure formed by the column of liquid present in the fermentor. In addition, the bubble size increases significantly throughout the fermentor as the pressure decreases with height. The increasing bubble diameter proportionately reduces the rate of mass transfer between the gas bubbles and the liquid phase by reducing the ratio of gas bubble area (proportionate to the square of the gas bubble radius) to gas bubble volume (proportionate to the cube of the gas bubble radius) through which mass transfer may occur. Flow rates and shear forces in airlift fermentors are significantly lower than in stirred tank fermentors, which also tend to increase bubble coalescence and reduce the efficiency of cooling the fermentor. Finally, separation of the unused and waste gases from the mixture exiting the upflow portion of the fermentor prior to the return of the liquid to the downflow section can be challenging.

Loop reactors are described in U.S. Pat. No. 7,575,163 and have been proposed for fermenting microorganisms, e.g., for the generation of biomass or for the preparation of materials produced by microorganisms. FIG. 1 of U.S. Pat. No. 7,575,163 illustrates one loop reactor 1 including an effluent gas removal zone 2 which flows into a vertical downflow zone 3. Effluent gas removal zone 2 includes an outlet port 7 and an emergency vent 8. Vertical downflow zone 3 includes a nutrient gas inlet 15. A propeller 10 powered by motor 11 assists in circulation of a liquid culture medium through the loop reactor. Upstream of propeller 10 is an exit port 12 for removing material from the loop reactor. Downstream of propeller 10 are ammonia and mineral inlets 17 and 18. Liquid culture medium 9 passes through a plurality of static mixers 14 in a horizontal section 4 of the loop reactor. The horizontal section of the loop reactor also includes a plurality of nutrient gas inlets 13. Downstream of the last static mixer 14, the loop reactor includes a vertical upflow section 5. The top end of vertical upflow section 5 fluidly communicates with a substantially horizontal outflow zone 6. Vertical upflow section 5 is provided with a nutrient gas inlet 16. Upstream of nutrient gas inlet 16 is a drive gas inlet 19 through which a driving gas is delivered to the liquid culture medium. The '163 patent describes the substantially horizontal outflow zone 6 is desirable from the standpoint of making degassing of an effluent gas/liquid culture medium particularly effective.

BRIEF SUMMARY

In one aspect, the present disclosure describes systems, processes and apparatuses for efficient mass transfer of gaseous substrates for microbial fermentation. Additionally, this disclosure describes systems, processes and apparatuses for fermenting gaseous carbon-containing feedstocks using a culture primarily comprising a $C_1$ metabolizing non-photosynthetic microorganism. In other aspects, this disclosure describes systems, processes and apparatuses for fermenting gaseous feedstocks which include gaseous substrates, using other than $C_1$ metabolizing non-photosynthetic microorganism(s). In yet another aspect, this disclosure describes scalable fermentor designs for allowing high flux gas-phase to liquid-phase mass transfer in addition to efficient gas/liquid separation and gas removal. Systems and processes for fermentation that overcome disadvantages known in the art and provide the public with new and safe processes and devices for the optimal production of a variety of products are described.

Such fermentation systems may employ one or more species of microorganism that are capable of metabolizing gaseous compounds; for example, $C_1$ compounds. Such microorganisms include prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* or *Pseudomonas*. In some instances, the $C_1$ metabolizing microorganisms may include methanotrophs, methylotrophs or combinations thereof. Preferred methanotrophs include *Methylomonas, Methylobacter, Methylococcus, Methylosinus, Methylocystis, Methylomicrobium, Methanomonas,* or combinations thereof. Exemplary methanotrophs include *Methylomonas* sp. 16a (ATCC PTA 2402), *Methylosinus trichosporium* (NRRL B-II, 196), *Methylosinus sporium* (NRRL B-II, 197), *Methylocystis parvus* (NRRL B-II, 198), *Methylomonas methanica* (NRRL B-5 11, 199), *Methylomonas alb us* (NRRL B-II, 200), *Methylobacter capsulatus* (NRRL B-11, 201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum* 20Z, or high growth variants thereof. Preferred methylotrophs include *Methylobacterium extorquens, Methylobacterium radiotolerans, Methylobacterium populi, Methylobacterium chloromethanicum, Methylobacterium nodulans,* or combinations thereof.

Microorganisms capable of metabolizing $C_1$ compounds found in syngas include, but are not limited to *Clostridium, Moorella, Pyrococcus, Eubacterium, Desulfobacterium, Carboxydothermus, Acetogenium, Acetobacterium, Acetoanaerobium, Butyribacterium, Peptostreptococcus,* or combinations thereof. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen,* or combinations thereof. In some instances, $C_1$ metabolizing microorganisms are eukaryotes such as yeast, including *Candida, Yarrowia, Hansenula, Pichia, Torulopsis,* or *Rhodotorula*.

In other instances, the $C_1$ metabolizing non-photosynthetic microorganism is an obligate $C_1$ metabolizing non-photosynthetic microorganism, such as an obligate methanotroph, an obligate methylotroph, or combinations thereof. In some instances, the $C_1$ metabolizing non-photosynthetic microorganism is a recombinant microorganism comprising a heterologous polynucleotide encoding a fatty acid producing enzyme, a formaldehyde assimilation enzyme, or combinations thereof.

In addition to the above, the present disclosure describes the following embodiments. A first embodiment directed to a system for stimulating production of biomass that includes a loop reactor which includes a fluid moving device having an inlet and an outlet with the inlet of the fluid moving device in fluid communication with an outlet of a substantially vertical downflow zone. The loop reactor includes a loop section including an outlet and an inlet, the inlet of the loop section in fluid communication with the outlet of the fluid moving device and a substantially vertical upflow zone including an outlet and an inlet with the inlet of the vertical upflow zone in fluid communication with the outlet of the loop section. The loop reactor further includes a gas/liquid separation vessel having a longitudinal axis and including an outlet, an inlet wherein the inlet of the gas/liquid separation vessel is located in a lower portion of the gas/liquid separation vessel and in fluid communication with the outlet of the substantially vertical upflow zone. The outlet of the horizontal gas/liquid separation vessel is in fluid communication with the inlet of the substantially vertical downflow zone. The gas/liquid separation vessel includes an intermediate section between the outlet and the inlet of the gas/liquid separation vessel with the intermediate section having a constant diameter D, an outlet side section on one side of the intermediate section, the outlet side section including the outlet of the gas/liquid separation vessel and an inlet side section on a side of the intermediate section opposite the outlet side section, the inlet side section including the inlet of the gas/liquid separation vessel and having a shape of an oblique conical frustum with an increasing diameter in a direction of fluid flow through the inlet side section. The system also includes a fluid conduit of non-increasing diameter extending between the outlet of the gas/liquid separation vessel and the inlet of the fluid moving device.

A second embodiment disclosed herein is directed to the first embodiment further including a drain conduit including in inlet end and an outlet end, the inlet end of the drain conduit connected to the outlet side section of the gas/liquid separation vessel and the outlet end of the drain conduit connected to the substantially vertical downflow zone.

A third embodiment disclosed herein is directed to the system of the first and second embodiments, wherein a lowermost edge of the inlet, the outlet, the intermediate section, the outlet side section and the inlet side section of the gas/liquid separation vessel contact a common plane.

A fourth embodiment disclosed herein is directed to the first through third embodiments further comprising a feed conduit including an inlet and an outlet, the inlet of the feed conduit connected to the substantially vertical upflow zone and the outlet end of the feed conduit connected to the inlet side section of the gas/liquid separation vessel.

A fifth embodiment disclosed herein is directed to the first through fourth embodiments wherein the inlet side section has a shape of an oblique conical frustum which includes a cone angle that ranges between 5 to 30°.

A sixth embodiment disclosed herein is directed to the first through fifth embodiment wherein the outlet of the gas/liquid separation vessel has a diameter that is less than a diameter of the inlet of the gas/liquid separation vessel.

A seventh embodiment disclosed herein is directed to the first through sixth embodiments wherein the inlet side section has a length measured along the longitudinal axis of the gas/liquid separation vessel that is greater than a length of the intermediate section measured along the longitudinal axis of the gas/liquid separation vessel and greater than a length of the outlet side section measured along the longitudinal axis of the gas/liquid separation vessel.

An eighth embodiment disclosed herein is directed to the first through seventh embodiments wherein the outlet side section has a dished shape.

A ninth embodiment disclosed herein is directed to a gas/liquid separation vessel that includes an outlet, an inlet, and a longitudinal axis, with the inlet of the gas/liquid separation vessel located in a lower portion of the gas/liquid separation vessel. The gas/liquid separation vessel includes an intermediate section between the outlet and the inlet of the gas/liquid separation vessel with the intermediate section having a constant diameter equal to D. An outlet side section is provided on one side of the intermediate section, the outlet side section including the outlet of the gas/liquid separation vessel. An inlet side section is provided on a side of the intermediate section opposite the outlet side section with the inlet side section including the inlet of the gas/liquid separation vessel and having a shape of an oblique conical frustum with an increasing diameter in a direction of fluid flow through the inlet side section.

A tenth embodiment described herein is directed to the ninth embodiment wherein a lowermost edge of the inlet, the outlet, the intermediate section, the outlet side section and the inlet side section of the gas/liquid separation vessel contact a common plane.

An eleventh embodiment described herein is directed to the ninth and tenth embodiments wherein the inlet side section has a shape of an oblique conical frustum includes a cone angle that ranges between 5 to 30°.

A twelfth embodiment described herein is directed to the ninth through eleventh embodiments wherein the outlet of the gas/liquid separation vessel has a diameter that is less than a diameter of the inlet of the gas/liquid separation vessel.

A thirteenth embodiment described herein is directed to the ninth through twelfth embodiments wherein the inlet side section has a length measured along the longitudinal axis of the gas/liquid separation vessel that is greater than a length of the intermediate section measured along the longitudinal axis of the gas/liquid separation vessel and greater than a length of the outlet side section measured along the longitudinal axis of the gas/liquid separation vessel.

A fourteenth embodiment described herein is directed to the ninth through thirteenth embodiments, wherein the outlet side section has a dished shape.

A fifteenth embodiment described herein is directed to a process for stimulating production of biomass that includes the steps of flowing through a loop section of a loop reactor, a multi-phase mixture of a gas and a liquid culture medium, introducing nutrients into the multi-phase mixture, introducing methane and oxygen into the multi-phase mixture, separating the multi-phase mixture of a gas and a liquid culture medium into a gas phase and a liquid phase in a gas/liquid separation vessel. Separating the multi-phase mixture into a gas phase and a liquid phase in the gas/liquid separation vessel including the steps of flowing the multi-phase mixture of a gas and a liquid culture medium into a lower portion of the gas/liquid separation vessel through an inlet side section of the gas/liquid separation vessel wherein the inlet side section of the gas/liquid separation vessel has a shape of an oblique conical frustum and an increasing diameter in a direction of flow of the multi-phase mixture through the inlet side section; flowing the multi-phase mixture through an intermediate section located between an outlet side section of the gas/liquid separation vessel and the inlet side section of the gas/liquid separation vessel with the intermediate section having a constant diameter; and removing the liquid phase from an outlet of the gas/liquid separation vessel and delivering the removed liquid phase to an inlet of the loop section.

A sixteenth embodiment described herein is directed to the fifteenth embodiment wherein delivering the removed liquid phase to the inlet of the loop section includes flowing the removed liquid phase through a conduit of non-increasing diameter.

A seventeenth embodiment described herein is directed to the sixteenth embodiment wherein separating the multi-phase mixture of a gas and a liquid culture medium into a gas phase and a liquid phase in the gas/liquid separation vessel further includes flowing the multi-phase mixture through the inlet side section and the intermediate section of the gas/liquid separation vessel, the inlet side section and the intermediate section including a lowermost edge that contacts a common plane.

BRIEF DESCRIPTION OF THE SEVERAL VIEWS OF THE DRAWINGS

In the drawings, the sizes and relative positions of elements in the drawings are not necessarily drawn to scale. For example, the various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been selected solely for ease of recognition in the drawings.

FIG. 10 shows a high level flow diagram of a fermentation process that includes flowing a multi-phase mixture through a loop reactor according to one or more illustrated and/or described embodiments.

DETAILED DESCRIPTION

Figure 1:
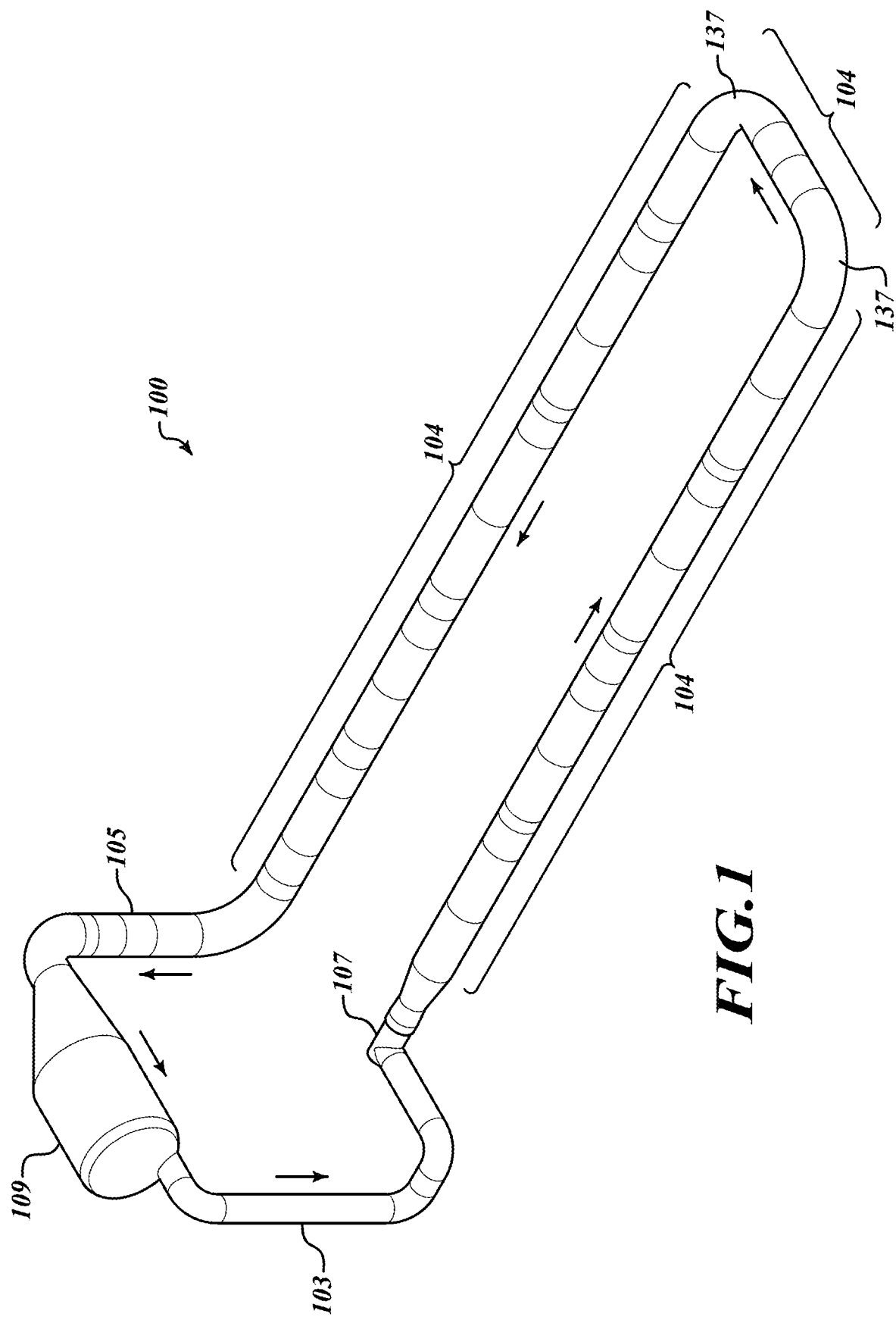
FIG. 1 shows a schematic view of a system for stimulating production of biomass according to one or more described embodiments.

In the following description, certain specific details are set forth in order to provide a thorough understanding of various embodiments. However, one skilled in the art will understand that the invention may be practiced without these details. In other instances, structures, standard vessel design details, detailed design parameters of available components such as liquid or gas distributors, pumps, turbines, and similar, details concerning the design and construction of American Society of Mechanical Engineers (ASME) pressure vessels, control system theory, specific steps in one or more fermentation processes, and the like have not been shown or described in detail to avoid unnecessarily obscuring descriptions of the described embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

Fermentors are generally defined as any vessel in which a fermentation process is carried out. Given the vast number of fermentation processes and the wide variety of fermentable substrates, fermentors can range from simple continuous stirred tank reactors found in the alcoholic beverage industry to highly complex, specialized vessels having gas distribution and internal structures tailored to a particular substrate and/or a particular biological species. Fermentors useful in converting carbon-containing gases such as methane and syngas (a mixture of CO and $H_2$) to longer chain gaseous and liquid hydrocarbons generally disperse a gas substrate containing the $C_1$ carbon compound within a liquid media containing one or more nutrients to provide a multi-phase mixture. This multi-phase mixture is fed to one or more microbiological colonies that convert a portion of the $C_1$ carbon compound(s) in the gas substrate to more preferred, longer chain, $C_2$ or higher compounds. The substrate composition, nutrients, and microbiological organisms comprising the colony (i.e., the biomass within the fermentor) can be variously adjusted or tailored to provide a desired final matrix of $C_2$ or higher compounds which may be present as a liquid, gas, or intracellular material.

Fermentors useful in utilizing carbon-containing gases such as methane and syngas (a mixture of CO and $H_2$) as a substrate for culturing single cell microorganisms such as fungi, yeasts and bacteria which contain high proportions of proteins generally disperse a gas substrate containing a $C_1$ carbon compound within a liquid media containing one or more nutrients to provide a multi-phase mixture. This multi-phase mixture is contacted with one or more microbiological colonies that convert a portion of the $C_1$ carbon compound(s) in the gas substrate to proteins. The substrate composition, nutrients, and microbiological organisms comprising the colony (i.e., the biomass within the fermentor) can be variously adjusted or tailored to provide a desired final matrix of protein-containing biomass.

From a mass transfer perspective, gas substrate fermentors present a unique challenge in that the substrate is trapped within a gas bubble and in order for microbiological uptake of the substrate to occur, the gas substrate must first pass from the gas bubble to the microbiological organisms either directly or indirectly via dissolution in the liquid media. Such fermentation processes are thus frequently limited by the ability of the system to facilitate and/or sustain a desirably high level of mass transfer of the substrate from the gas bubbles to the microbiological organisms within the fermentor. At the least, the rate of mass transfer from the gas bubble to either the surrounding liquid media or to a microbiological organisms is a function of the gas pressure within the gas bubble, the volume to surface area ratio of the gas bubble, and the contact time of the gas bubble with the surrounding liquid or microbiological organisms. Increasing the pressure within the gas bubble or increasing the contact time of the gas bubble with the surrounding liquid or microbiological organisms results in a higher effective mass transfer rate between the substrate and the microbiological organisms. Decreasing the volume to surface area ratio of the gas bubble (i.e., reducing the diameter of the gas bubbles) results in a higher effective mass transfer rate between the gas bubble and the surrounding liquid. Preferred fermentors from a mass transfer standpoint would therefore generate a large number of relatively small diameter gas bubbles at a relatively high pressure that are held in close or intimate contact with the surrounding liquid or microbiological organisms for an extended period of time.

Disclosed herein are a number of fermentation systems, methods, and apparatuses that are capable of providing relatively small diameter, relatively high pressure gas bubbles. Disclosed herein are a number of fermentation systems, methods, and apparatuses capable of providing an extended contact time with the surrounding liquid and/or biological organism(s). Such fermentation systems, methods, and apparatuses can advantageously provide a highly efficient gas substrate fermentation system that may be particularly useful in converting $C_1$ compounds to more preferred gaseous, liquid, and intra-cellular $C_2$ and higher compounds or stimulating the growth of microorganisms containing high proportions of protein.

As used herein, the terms "$C_1$ substrate" or "$C_1$ compound" refer to any carbon-containing molecule or composition that lacks a carbon-carbon bond. Sample $C_1$ molecules or compositions include methane, methanol, formaldehyde, formic acid or a salt thereof, carbon monoxide, carbon dioxide, syngas, methylamines (e.g., monomethylamine, dimethylamine, trimethylamine), methylthiols, or methylhalogens.

As used herein, the term "microorganism" refers to any microorganism having the ability to use a gaseous substrate as a source of energy or as its sole source of energy and biomass, and may or may not use other carbon substrates (such as sugars and complex carbohydrates) for energy and biomass. Examples of microorganisms as used herein include the heterotrophic bacteria *Ralstonia* sp. (formerly *Alcaligenes acidovorans*) DB3 (strain NCIMB 13287), *Brevibacillus agri* (formerly *Bacillus firmus*) DB5 (strain NCIMB 13289) and *Aneurinibacillus* sp. (formerly *Bacillus brevis*) DB4 (strain NCIMB 13288) which each have optimum growth at a temperature of about 45° C. *Ralstonia* sp. DB3 is a gram-negative, aerobic, motile rod belonging to the family Pseudomonadaceae which can use ethanol, acetate, propionate and butyrate for growth. *Aneurinibacillus* sp. DB4 is a gram-negative, endospore-forming, aerobic rod belonging to the genus *Bacillus* which can utilize acetate, D-fructose, D-mannose, ribose and D-tagatose. *Brevibacillus agri* DB5 is a gram-negative, endospore-forming, motile, aerobic rod of the genus *Bacillus* which can utilize acetate, N-acetyl-glucosamine, citrate, gluconate, D-glucose, glycerol and mannitol. Suitable yeasts for use in the processes of the invention may be selected from the group consisting of *Saccharomyces* and *Candida*.

If desired, the processes described herein may be performed using bacteria (or yeasts) genetically modified so as to generate a desired chemical compound which can then be extracted from the intercellular fluid or the biomass harvested from the reactor. The scientific and patent literature contains numerous examples of such genetically modified microorganisms including, inter alia, methanotrophic bacteria.

In at least some instances in accordance with embodiments described herein, the microbiological organisms used to ferment gaseous carbon-containing feedstocks employ a culture primarily comprising a $C_1$ metabolizing non-photosynthetic microorganism. Such fermentation systems may use one or more species of $C_1$ metabolizing microorganisms that are prokaryotes or bacteria, such as *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* or *Pseudomonas*. In some instances, the $C_1$ metabolizing bacteria may include a methanotroph or a methylotroph. Preferred methanotrophs include *Methylomonas, Methylobacter, Methylococcus, Methylosinus, Methylocystis, Methylomicrobium, Methanomonas,* or a combination thereof. Exemplary methanotrophs include *Methylomonas* sp. 16a (ATCC PTA 2402), *Methylosinus trichosporium* (NRRL B-II, 196), *Methylosinus sporium* (NRRL B-II, 197), *Methylocystis parvus* (NRRL B-II, 198), *Methylomonas methanica* (NRRL B-5 11, 199), *Methylomonas alb us* (NRRL B-II, 200), *Methylobacter capsulatus* (NRRL B-11,201), *Methylobacterium organophilum* (ATCC 27,886), *Methylomonas* sp. AJ-3670 (FERM P-2400), *Methylomicrobium alcaliphilum, Methylocella silvestris, Methylacidiphilum infernorum, Methylibium petroleiphilum, Methylosinus trichosporium* OB3b, *Methylococcus capsulatus* Bath, *Methylomonas* sp. 16a, *Methylomicrobium alcaliphilum* 20Z, or a high growth variants thereof. Preferred methylotrophs include *Methylobacterium extorquens, Methylobacterium radiotolerans, Methylobacterium populi, Methylobacterium chloromethanicum, Methylobacterium nodulans,* or a combination thereof.

Microorganisms capable of metabolizing $C_1$ compounds found in syngas include, but are not limited to *Clostridium, Moorella, Pyrococcus, Eubacterium, Desulfobacterium, Carboxydothermus, Acetogenium, Acetobacterium, Acetoanaerobium, Butyribacterium, Peptostreptococcus,* or combinations thereof may also be used. Exemplary methylotrophs include *Clostridium autoethanogenum, Clostridium ljungdahli, Clostridium ragsdalei, Clostridium carboxydivorans, Butyribacterium methylotrophicum, Clostridium woodii, Clostridium neopropanologen,* or a combination thereof. In some instances, $C_1$ metabolizing microorganisms are eukaryotes such as yeast, including *Candida, Yarrowia, Hansenula, Pichia, Torulopsis,* or *Rhodotorula*.

In other instances, the $C_1$ metabolizing non-photosynthetic microorganism is an obligate $C_1$ metabolizing non-photosynthetic microorganism, such as an obligate methanotroph or methylotroph. In some instances, the $C_1$ metabolizing non-photosynthetic microorganism is a recombinant microorganism comprising a heterologous polynucleotide encoding a fatty acid producing enzyme, a formaldehyde assimilation enzyme, or a combination thereof.

As used herein, the terms "$C_1$ metabolizing microorganism" or "$C_1$ metabolizing non-photosynthetic microorganism" refer to any microorganism having the ability to use a single carbon ($C_1$) substrate as a source of energy or as its sole source of energy and biomass, and may or may not use other carbon substrates (such as sugars and complex carbohydrates) for energy and biomass. For example, a $C_1$ metabolizing microorganism may oxidize a $C_1$ substrate, such as methane or methanol. $C_1$ metabolizing microorganisms include bacteria (such as Methanotrophs and Methylotrophs) and yeast. In at least some instances, a $C_1$ metabolizing microorganism does not include a photosynthetic microorganism, such as algae. In certain embodiments, the $C_1$ metabolizing microorganism will be an "obligate $C_1$ metabolizing microorganism," meaning its sole source of energy comprises $C_1$ substrates and nothing else.

As used herein, the term "methylotrophic bacteria" refers to any bacteria capable of oxidizing organic compounds that do not contain carbon-carbon bonds. In certain embodiments, a methylotrophic bacterium may be a methanotroph. For example, "methanotrophic bacteria" refers to any methylotrophic bacteria having the ability to oxidize methane as its primary source of carbon and energy. Exemplary methanotrophic bacteria include *Methylomonas, Methylobacter, Methylococcus, Methylosinus, Methylocystis, Methylomicrobium,* or *Methanomonas*. In certain other embodiments, the methylotrophic bacterium is an "obligate methylotrophic bacterium," which refers to bacteria that are limited to the use of $C_1$ substrates for the generation of energy.

In one specific embodiment of the invention, the process is performed using methanotrophic bacteria of the type described in WO 02/18617 to produce carotenoids, e.g., antheraxanthin, adonixanthin, astaxanthin, canthaxanthin, zeaxanthin and the other carotenoids mentioned on pages 39 and 40 of WO 02/18617. To this end, the methanotrophic bacterium *Methylomonas* 16a (ATCC PTA 2402) may particularly suitably be used. Carotenoids produced in this way may be separated out from the liquid culture medium as described in WO 02/18617, WO 02/20728 and WO 02/20733.

As used herein, the term "syngas" refers to a mixture including at least carbon monoxide (CO) and hydrogen ($H_2$). In at least some instances, syngas may also include $CO_2$, methane, and other gases in smaller quantities relative to CO and $H_2$. Syngas may be prepared using any available process, including but not limited to, a water gas shift or coal gasification process.

As used herein, the term "growth" is defined as any increase in cell mass. This may occur through cell division (replication) and the formation of new cells during "balanced growth," or during "unbalanced growth" when cellular mass increases due to the accumulation of one or more intracellular or intercellular polymers, such as certain lipids. In the latter case, growth may be manifest as an increase in cell size due to the accumulation of a biopolymer within the cell. During "balanced cell growth," all of the feedstocks (electron donors and electron acceptors) and all of the nutrients are present in the ratios required to make all of the macromolecular components of a cell. That is, no feedstock or nutrient limits the synthesis of proteins, complex carbohydrate polymers, fats, or nucleic acids. In contrast, during "unbalanced cell growth," a feedstock or nutrient needed to make one or more of a cell's macromolecules is not present in an amount or ratio required for balanced growth. Accordingly, this feedstock or nutrient becomes limiting and is referred to as a "limiting nutrient."

Some cells may still achieve net growth under unbalanced conditions, but the growth is unbalanced and polymers that can be synthesized in the absence of the limiting feedstock or nutrient will accumulate. These polymers include lipids or intracellular storage products, such as the polyhydroxyalkanoates (PHAs), including polyhydroxybutyrate (PHB), polyhydroxyvalerate (PHV), and polyhydroxyhexanoate (PHHx)-glycogen, or secreted materials, such as extracellular polysaccharide. Such oil compositions are useful in the production of bioplastics.

Sample balanced and unbalanced growth conditions may differ in the nitrogen content in the media. For example, nitrogen constitutes about 12% of dry cell weight, which means that 12 mg/L nitrogen must be supplied (along with a feedstock and other nutrients in the required stoichiometric ratios) to grow 100 mg/L dry cell weight. If other feedstock and nutrients are available in the quantities needed to produce 100 mg/L of dry cell weight, but less than 12 mg/L nitrogen is provided, then unbalanced cell growth may occur, with accumulation of polymers that do not contain nitrogen. If nitrogen is subsequently provided, the stored polymer may serve as feedstock for the cell, allowing balanced growth, with replication and production of new cells.

As used herein, the term "growth cycle" as applied to a cell or microorganism refers to the metabolic cycle through which a cell or microorganism moves in culture conditions. For example, the cycle may include various stages, such as a lag phase, an exponential phase, the end of exponential phase, and a stationary phase.

As used herein, the term "exponential growth," "exponential phase growth," "log phase" or "log phase growth" refer to the rate at which microorganisms are growing and dividing. For example, during log phase, microorganisms are growing at their maximal rate given their genetic potential, the nature of the medium, and the conditions under which they are grown. Microorganism rate of growth is constant during exponential phase and the microorganism divides and doubles in number at regular intervals. Cells that are "actively growing" are those that are growing in log phase. In contrast, "stationary phase" refers to the point in the growth cycle during which cell growth of a culture slows or even ceases.

As used herein, the term "high growth variant" refers to an organism, microorganism, bacterium, yeast, or cell capable of growth with a $C_1$ substrate, such as methane or methanol, as the sole carbon and energy source and which possesses an exponential phase growth rate that is faster than the parent, reference or wild-type organism, microorganism, bacterium, yeast, or cell—that is, the high growth variant has a faster doubling time and consequently a high rate of growth and yield of cell mass per gram of $C_1$ substrate metabolized as compared to a parent cell (see, e.g., U.S. Pat. No. 6,689,601).

As used herein, the term "biofuel" refers to a fuel at least partially derived from "biomass."

As used herein, the term "biomass" or "biological material" refers to organic material having a biological origin, which may include one or more of whole cells, lysed cells, extracellular material, or the like. For example, the material harvested from a cultured microorganism (e.g., bacterial or yeast culture) is considered the biomass, which can include cells, cell membranes, cell cytoplasm, inclusion bodies, products secreted or excreted into the culture medium, or any combination thereof. In certain embodiments, biomass comprises the $C_1$ metabolizing microorganisms of this disclosure together with the media of the culture in which the $C_1$ metabolizing microorganisms of this disclosure were grown. In other embodiments, biomass comprises $C_1$ metabolizing microorganisms (whole or lysed or both) of this disclosure recovered from a culture grown on a $C_1$ (e.g., natural gas, methane). In still other embodiments, biomass comprises the spent media supernatant or gases excreted or secreted from a culture of $C_1$ metabolizing microorganism culture on a $C_1$ substrate. Such a culture may be considered a renewable resource.

As used herein, the term "biorefinery" refers to a facility that integrates biomass conversion processes and equipment to produce fuels from biomass.

As used herein, "oil composition" refers to the lipid content of a biomass (e.g., bacterial culture), including fatty acids, fatty acid esters, triglycerides, phospholipids, poly hydroxyalkanoates, isoprenes, terpenes, or the like. In oil composition of a biomass may be extracted from the rest of the biomass materials, such as by hexane or chloroform extraction. In addition, an "oil composition" may be found in any one or more areas of a culture, including the cell membrane, cell cytoplasm, inclusion bodies, secreted or excreted into the culture medium, or any combination thereof. An oil composition is neither natural gas nor crude petroleum.

As used herein, the term "refinery" refers to an oil refinery, or aspects thereof, at which oil compositions (e.g., biomass, biofuel, or fossil fuels such as crude oil, coal or natural gas) may be processed. Sample processes carried out at such refineries include cracking, transesterification, reforming, distilling, hydroprocessing, isomerization, or any combination thereof.

As used herein, the terms "recombinant" or "non-natural" refer to an organism microorganism, cell, nucleic acid molecule, or vector that has at least one genetic alteration or has been modified by the introduction of a heterologous nucleic acid molecule, or refers to a cell that has been altered such that the expression of an endogenous nucleic acid molecule or gene can be controlled. Recombinant also refers to a cell that is derived from a cell having one or more such modifications. For example, recombinant cells may express genes or other nucleic acid molecules that are not found in identical form within the native cell (i.e., unmodified or wild type cell), or may provide an altered expression pattern of endogenous genes, such genes that may otherwise be over-expressed, under-expressed, minimally expressed, or not expressed at all. In another example, genetic modifications to nucleic acid molecules encoding enzymes or functional fragments thereof can provide biochemical reaction(s) or metabolic pathway capabilities to a recombinant microorganism or cell that is new or altered from its naturally occurring state.

As used herein, the term "heterologous" nucleic acid molecule, construct or sequence refers to a nucleic acid molecule or portion of a nucleic acid molecule sequence that is not native to a cell in which it is expressed or is a nucleic acid molecule with an altered expression as compared to the native expression levels in similar conditions. For example, a heterologous control sequence (e.g., promoter, enhancer) may be used to regulate expression of a gene or a nucleic acid molecule in a way that is different than the gene or a nucleic acid molecule is normally expressed in nature or culture. Generally, heterologous nucleic acid molecules are not endogenous to the cell or part of the genome in which they are present, and have been added to the cell by conjugation, transformation, transfection, electroporation, or the like.

As used herein, the term "vertical" refers to a direction that is aligned with the gravity vector at the location in question.

As used herein, the term "horizontal" refers to a direction that is perpendicular to the gravity vector at the location in question.

As used herein, the phrase "substantially vertical" refers to direction that is less than 20° from vertical.

As used herein, the phrase "substantially horizontal" refers to a direction that is less than 20° from horizontal.

As used herein, the term "dished" refers to elliptical dished heads or ends of the type used with pressure vessels, dished heads that meet ASME standards such as ASME 80:10 and standard flanged heads. A dished head or end is not conical.

The systems for fermentation of the instant disclosure may include separate units (e.g., processing units or systems that are disposed in close proximity or adjacent to each other, or not), integrated units, or the system itself may be interconnected and integrated. The systems of this disclosure may use at least one gas phase feedstock, including one or more $C_1$ compounds, oxygen, and/or hydrogen. In certain embodiments, the fermentation system uses a $C_1$ metabolizing microorganism (e.g., a methanotroph such as *Methylosinus trichosporium* OB3b, *Methylococcus capsulatus* Bath, *Methylomonas* sp. 16a, *Methylomicrobium alcaliphilum* 20Z, or high growth variants or combinations thereof) as the primary microorganism in the fermentation culture.

A variety of culture methodologies may be used for the microorganism, bacteria and yeast described herein. For example, $C_1$ metabolizing microorganisms, such as methanotroph or methylotroph bacteria, may be grown by batch culture and continuous culture methodologies. Generally cells in log phase are often responsible for the bulk production of a product or intermediate of interest in some systems, whereas stationary or post-exponential phase production can be obtained in other systems.

A classical batch culturing method is a closed system in which the media composition is set when the culture is started and is not altered during the culture process. That is, media is inoculated at the beginning of the culturing process with one or more microorganisms of choice and then is allowed to grow without adding additional microorganisms to the system. As used herein, a "batch" culture is in reference to not changing the amount of a particular carbon source initially added, whereas control of factors such as pH and oxygen and/or hydrogen concentration can be monitored and altered during the culture. In batch systems, metabolite and biomass compositions of the system change constantly up to the time the culture is terminated. Within batch cultures, cells (e.g., bacteria such as methylotrophs) will generally move from a static lag phase to a high growth logarithmic phase to a stationary phase where growth rate is reduced or stopped (and will eventually lead to cell death if conditions do not change).

A fed-batch system is a variation on the standard batch system in which a carbon substrate of interest is added in increments as the culture progresses. Fed-batch systems are useful when cell metabolism is likely to be inhibited by catabolite repression and when it is desirable to have limited amounts of substrate in the media. Since it is difficult to measure actual substrate concentration in fed-batch systems, an estimate is made based on changes of measurable factors such as pH, dissolved oxygen, and the partial pressure of waste gases. Batch and fed-batch culturing methods are common and known in the art (see, e.g., Thomas D. Brock, Biotechnology: A Textbook of Industrial Microbiology, 2nd Ed. (1989) Sinauer Associates, Inc., Sunderland, Mass.; Deshpande, 1992, Appl. Biochem. Biotechnol. 36:227).

Continuous cultures are "open" systems in the sense that defined culture media is continuously added to a bioreactor while an equal amount of used ("conditioned") media is removed simultaneously for processing. Continuous cultures generally maintain the cells at a constant high, liquid phase density where cells are primarily in logarithmic growth phase. Alternatively, continuous culture may be practiced with immobilized cells (e.g., biofilm) where carbon and nutrients are continuously added and valuable products, by-products, and waste products are continuously removed from the cell mass. Cell immobilization may be achieved with a wide range of solid supports composed of natural materials, synthetic materials, or a combination thereof.

Continuous or semi-continuous culture allows for the modulation of one or more factors that affect cell growth or end product concentration. For example, one method may maintain a limited nutrient at a fixed rate (e.g., carbon source, nitrogen) and allow all other parameters to change over time. In other embodiments, several factors affecting growth may be continuously altered while cell concentration, as measured by media turbidity, is kept constant. The goal of a continuous culture system is to maintain steady state growth conditions while balancing cell loss due to media being drawn off against the cell growth rate. Methods of modulating nutrients and growth factors for continuous culture processes and techniques for maximizing the rate of product formation are well known in the art (see Brock, 1992).

In certain embodiments, culture media includes a carbon substrate as a source of energy for a $C_1$ metabolizing microorganism. Suitable substrates include $C_1$ substrates, such as methane, methanol, formaldehyde, formic acid (formate), carbon monoxide, carbon dioxide, methylated amines (methylamine, dimethylamine, trimethylamine, etc.), methylated thiols, or methyl halogens (bromomethane, chloromethane, iodomethane, dichloromethane, etc.). In certain embodiments, culture media may comprise a single $C_1$ substrate as the sole carbon source for a $C_1$ metabolizing microorganism, or may comprise a mixture of two or more $C_1$ substrates (mixed $C_1$ substrate composition) as multiple carbon sources for a $C_1$ metabolizing microorganism.

Additionally, some $C_1$ metabolizing organisms are known to utilize non-$C_1$ substrates, such as sugar, glucosamine or a variety of amino acids for metabolic activity. For example, some *Candida* species can metabolize alanine or oleic acid (Sulter et al., Arch. Microbiol. 153:485-489, 1990). *Methylobacterium extorquens* AM1 is capable of growth on a limited number of $C_2$, $C_3$, and $C_4$ substrates (Van Dien et al., Microbiol. 149:601-609, 2003). Alternatively, a $C_1$ metabolizing microorganism may be a recombinant variant having the ability to utilize alternative carbon substrates. Hence, it is contemplated that a carbon source in culture media may comprise a mixture of carbon substrates, with single and multi-carbon compounds, depending on the $C_1$ metabolizing microorganism selected.

In certain embodiments, the instant disclosure provides a method for making fuel, comprising converting biomass from a culture primarily comprising a $C_1$ metabolizing non-photosynthetic microorganism into an oil composition and refining the oil composition into a fuel. In certain embodiments, the $C_1$ metabolizing non-photosynthetic microorganism is an obligate $C_1$ metabolizing non-photosynthetic microorganism, such as an obligate methanotroph or methylotroph. In further embodiments, the $C_1$ metabolizing non-photosynthetic microorganism is a recombinant microorganism comprising a heterologous polynucleotide encoding a fatty acid producing enzyme, a formaldehyde assimilation enzyme, or a combination thereof. In further embodiments, the oil composition is derived or extracted from cell membrane of the $C_1$ metabolizing non-photosynthetic microorganism, such as a methylotroph or methanotroph.

In certain embodiments, the instant disclosure provides a method for making fuel by refining an oil composition in a refining unit to produce fuel, wherein the oil composition is derived from a $C_1$ metabolizing non-photosynthetic microorganism, such as a methylotroph or methanotroph. In further embodiments, the method further comprises use of a processing unit for extracting the oil composition from the $C_1$ metabolizing non-photosynthetic microorganism. In still further embodiments, the method comprises (a) culturing $C_1$ metabolizing bacteria in the presence of a feedstock comprising a $C_1$ substrate in a controlled culturing unit, wherein the cultured bacteria produces an oil composition; (b) extracting the oil composition from the cultured bacteria in a processing unit; and (c) refining the extracted oil composition in a refining unit to produce fuel. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural products, such as ethanol, acetate, butanol, single-cell protein, sugars, or other metabolites or cellular products wherein the natural product is derived from a $C_1$ metabolizing non-photosynthetic microorganism, such as a methylotroph or methanotroph.

In further embodiments, the method further comprises use of a processing unit for extracting the natural product from the $C_1$ metabolizing non-photosynthetic microorganism.

In still further embodiments, the method comprises (a) culturing $C_1$ metabolizing bacteria in the presence of a feedstock comprising a $C_1$ substrate in a controlled culturing unit, wherein the cultured bacteria produce a natural product; (b) extracting the natural product from the cultured bacteria in a processing unit; and (c) refining the natural product to produce a commercial product. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural or non-natural products, such as ethanol, acetate, butanol, isoprene, propylene, farnesene, enzymes, or other metabolites or cellular products wherein the product is derived from a genetically engineered $C_1$ metabolizing non-photosynthetic microorganism, such as a methylotroph or methanotroph which has been transformed with a heterologous nucleotide sequence. In further embodiments, the method further comprises use of a processing unit for extracting the product from the genetically engineered $C_1$ metabolizing non-photosynthetic microorganism. In still further embodiments, the method comprises (a) culturing genetically engineered $C_1$ metabolizing bacteria in the presence of a feedstock comprising a $C_1$ substrate in a controlled culturing unit, wherein the cultured bacteria produce a natural product; (b) extracting the natural product from the cultured bacteria in a processing unit; and (c) refining the natural product to produce a commercial product. In certain embodiments, the feedstock $C_1$ substrate is methane, methanol, formaldehyde, formic acid, carbon monoxide, carbon dioxide, a methylamine, a methylthiol, or a methylhalogen.

In certain embodiments, the instant disclosure provides a method for making natural or non-natural products, such as ethanol, acetate, butanol, isoprene, propylene, farnesene, enzymes, or other metabolites or cellular products wherein the product is derived from a non-$C_1$ metabolizing microorganism, such as *Escherichia coli, Saccaromyces cerevisiae*, or other common production microorganism. In certain embodiments, the feedstock substrate is glucose, sucrose, glycerol, cellulose or other multicarbon feedstocks.

An exemplary system for stimulating production of biomass in accordance with embodiments described herein includes a loop reactor 100 of the type illustrated in FIG. 1. Loop reactor 100 illustrated in FIG. 1 includes a substantially vertical downflow zone 103 and a substantially vertical upflow zone 105 separated by a substantially horizontal zone or loop section identified by the plurality of brackets 104. The outlet of substantially vertical downflow zone 103 is in fluid communication with an inlet of fluid moving device 107. The outlet of fluid moving device 107 is in fluid communication with the inlet of substantially horizontal zone 104. The outlet of substantially horizontal zone 104 is in fluid communication with the inlet of substantially vertical upflow zone 105. The outlet of substantially vertical upflow zone 105 is in fluid communication with an inlet of gas/liquid separation vessel 109. An outlet of gas/liquid separation vessel 109 is in fluid communication with the inlet of substantially vertical downflow zone 103 via a drain conduit having an inlet end connected to the gas/liquid separation vessel 109 and having an outlet end connected to the substantially vertical downflow zone 103. Specific embodiments of systems for stimulating production of biomass in accordance with embodiments described herein includes a fluid conduit of non-increasing diameter extending between the outlet of the gas/liquid separation vessel 109 and the inlet of fluid moving device 107. Fluid flows through loop reactor 100 in a clockwise direction (as indicated by the arrows) under the influence of fluid moving device 107.

Figure 2:
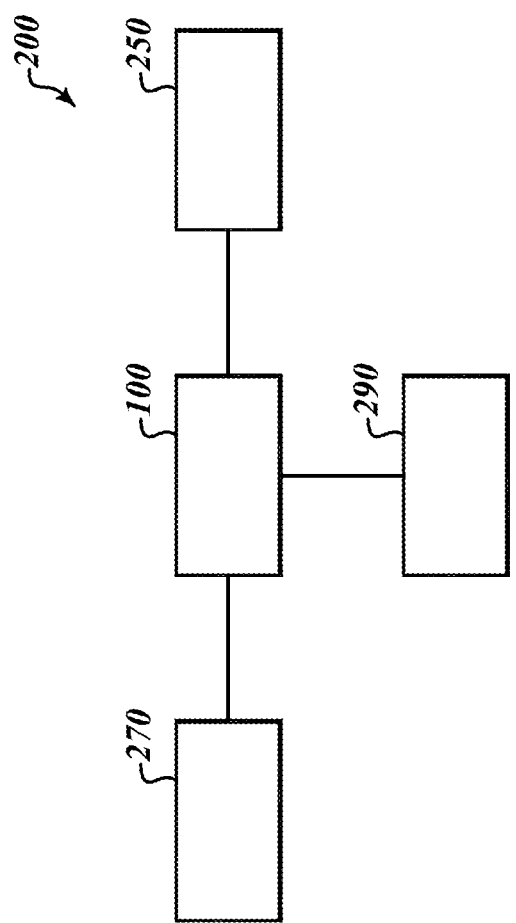
FIG. 2 shows a schematic block diagram of subsystems of a system for stimulating production of biomass according to one or more described embodiments.

FIG. 2 shows an exemplary system 200 for stimulating production of biomass that includes a loop reactor 100 along with an optional separation subsystem 250, an optional thermal subsystem 270 and optional control subsystem 290. Although shown as an integrated system 200, the optional subsystems may be installed or otherwise combined with the loop reactor 100 either individually or in any combination.

One or more liquids and one or more gas substrates are introduced to the loop reactor 100 to form a multi-phase mixture with a liquid culture media that travels through the loop reactor 100. After passage through the loop reactor 100, the multi-phase mixture may contain one or more compounds produced by the biological organisms within the loop reactor 100, unconsumed nutrients and other compounds in the liquid within the multi-phase mixture, unconsumed gases in the gas bubbles within the multi-phase mixture, and microbiological organisms in the form of biosolids. Excess microbiological organisms may be removed from the loop reactor 100 as biomass either intermittently or continuously. Biomass accumulations within the loop reactor 100 may be removed to maintain the overall biomass within the loop reactor 100 within a defined range or above or below a defined threshold. In at least some instances, biomass removed from the loop reactor 100 may include one or more useful compounds. For example, the biological organisms within the excess biomass may contain an amount of one or more intracellular lipids or similar compounds useful in the production of a biofuel such as biodiesel or protein-containing products.

The one or more liquids may include any liquid suitable for sustaining or delivering one or more nutrients to the microbiological organisms within the loop reactor 100. Such liquids may include, but are not limited to, solutions containing water, one or more alcohols, minerals, one or more nitrogen-containing compounds, one or more phosphorus-containing compounds, and the like. In at least some instances, one or more fluid movers are used to deliver the one or more liquids to the loop reactor 100 in a controlled manner and pressure. The one or more fluid movers can include any type of pump or similar device capable of transferring a liquid between two points. Example fluid movers include, but are not limited to, centrifugal pumps, positive displacement pumps, progressing cavity pumps, double diaphragm pumps, and the like. Other illustrative fluid movers include, but are not limited to eductors, ejectors, and similar devices. The transfer of liquid to the loop reactor 100 can be flow controlled, pressure controlled, or controlled using combinations of pressure, temperature, flow, level, flowrate, superficial velocity, or compositional analysis process variable data gathered from one or more points within the loop reactor 100 or from one or more points within the system 200. In at least some instances, the transfer of liquid by the fluid mover can be controlled based on the measured concentration of one or more components or compounds (e.g., one or more carbon-containing or nitrogen-containing nutrients) within the loop reactor 100; for example, the flow of liquid transferred by the fluid mover may be increased in response to a measured decrease in nutrient concentration within the loop reactor 100.

The one or more gas substrates can include any gas, gases, or combination of gases suitable for sustaining or delivering one or more nutrients to the biological organisms within the loop reactor 100. Such gases can include, but are not limited to, one or more gases containing carbon compounds. Such gases can include, but are not limited to, one or more gases containing $C_1$ carbon compounds such as methane or carbon monoxide. The one or more gas substrates may also include one or more gases used in the metabolic processes of the biological organisms within the loop reactor 100. Such gases can include, but are not limited to, oxygen, oxygen-containing compounds and hydrogen. The one or more gas substrates may be transferred to the loop reactor 100 as a pure gas or as a gas mixture (e.g., syngas, a mixture of carbon monoxide and hydrogen). The one or more gas substrates may be transferred to the loop reactor 100 individually (e.g., methane and an oxygen-containing gas such as air may be transferred individually to minimize the likelihood of formation of an explosive gas mixture external to the loop reactor 100).

The one or more gas substrates may optionally be transferred to the loop reactor 100 using a gas mover. Example gas movers include, but are not limited to, rotary lobe compressors, centrifugal compressors, screw compressors, and the like. The delivery pressure of the one or more gas substrates depends upon a variety of factors including the operating pressure of the loop reactor 100 and the pressure drop associated with the gas distributor used to distribute the one or more gas substrates within the loop reactor 100. Similarly, the delivery flowrate of the one or more gas substrates may be manually or automatically controlled to maintain the concentration or level of dissolved gas within the loop reactor 100 within a defined range (e.g., dissolved oxygen above at least 4 ppm) based at least in part on the needs of the biological organisms present in the loop reactor 100. In at least some instances, the one or more gas substrates can be delivered to the loop reactor 100 at a pressure of from about 5 psig to about 600 psig; from about 25 psig to about 400 psig; or from about 50 psig to about 300 psig.

Any number of gases may be introduced through a common gas distribution header or any number of individual gas distribution headers. Such gas distribution headers may introduce all of the gas substrate at a single point within the loop reactor 100 or may introduce portions of the gas substrate at various locations throughout the loop reactor 100. In at least some instances, the gas substrate can include, but is not limited to, methane, carbon monoxide, hydrogen, or oxygen. In at least some instances, the feed rate of the gas substrate can be referenced to the feed rate of the liquid media. For example, methane may be introduced as a gas substrate at a rate of from about 0.1 grams of methane/liter of liquid media (g/l) to about 100 g/l; from about 0.5 g/l to about 50 g/l; or from about 1 g/l to about 25 g/l. Carbon monoxide ("CO") may be introduced as a gas substrate 204 at a rate of from about 0.1 grams of CO/liter of liquid media (g/l) to about 100 g/l; from about 0.5 g/l to about 50 g/l; or from about 1 g/l to about 25 g/l. Oxygen may be introduced as a gas substrate 204 at a rate of from about 1 grams of oxygen/liter of liquid media (g/l) to about 100 g/l; from about 2 g/l to about 50 g/l; or from about 5 g/l to about 25 g/l. Hydrogen may be introduced as a gas substrate 204 at a rate of from about 0.01 grams of hydrogen/liter of liquid media (g/l) to about 50 g/l; from about 0.1 g/l to about 25 g/l; or from about 1 g/l to about 10 g/l.

Within the loop reactor 100 the microbiological organisms will metabolize at least a portion of the carbon-containing compounds present in the multi-phase mixture. At least a portion of this process may include the production of additional microbiological organisms that increase the overall quantity of biomass present in the loop reactor 100. Left uncontrolled, the biomass within the loop reactor 100 may accumulate to a point such that one or more operational aspects of the loop reactor 100 (e.g., flowrate, pressure drop, production of desired products, etc.) is compromised or adversely affected by the presence of the excess biomass. In such instances, the ability to remove at least a portion of the biomass present in the loop reactor 100 is desirable. In at least some instances, biomass preferentially accumulates at a location within a gas/liquid separation vessel (109 in FIGS. 3-9) facilitating biosolids removal from the loop reactor 100 via at least one biomass removal port provided in gas/liquid separation vessel 109 or at a different location or locations along loop reactor 100. The removed biomass can be delivered to separation subsystem 250 where the biomass can be further processed and desirable products recovered from the biomass.

In at least some instances, all or a portion of the biomass production process may be at least partially automatically controlled using a control subsystem 290. The control subsystem 290 may collect process-related information provided by one or more process elements in the form of signals containing analog or digital data representing one or more process variables. For instance, the control subsystem can collect process-related signals using one or more process elements including, but not limited to, mass flow sensors, volumetric flow sensors, temperature sensors, pressure sensors, level sensors, analytical sensors (e.g., dissolved oxygen sensors, methane sensors, ammonia sensors, biological oxygen demand or "BOD" sensors, pH sensors, conductivity sensors, and the like) or any other device capable of providing a signal containing data representative of one or more process-related conditions within the loop reactor 100.

The control subsystem 290 may execute one or more sets of instructions controlling, altering, or adjusting one or more aspects of the fermentation process based at least in part on the process variable signals received from the process elements. Such instructions may result in the generation of one or more control output signals by the control subsystem 290. The control output signals can be transmitted from the control subsystem 290 to one or more final control elements such as block valves, control valves, motors, variable speed drives, thermal energy sources or sinks, etc. The interaction between the final control elements and the fermentation process can, in turn, provide the control subsystem 290 with a high degree of relatively accurate control of the biomass production process.

For example, responsive to the receipt of one or more signals containing data indicative of the temperature of the multi-phase mixture in the loop reactor 100, the control subsystem 290 may initiate, alter, or cease the flow of thermal transfer media to a heat transfer unit operation. Similarly, responsive to the receipt of one or more signals containing data indicative of the dissolved oxygen level of the multi-phase mixture in the loop reactor 100, the control subsystem 290 may increase, decrease, or maintain the flow of the oxygen-containing gas substrate to the loop reactor 100. Although only two illustrative examples are provided herein, any flow, level, pressure, analytical value, or the like that is appropriate to the fermentation process may be similarly controlled by the control subsystem 290 using one or more appropriate process sensors and one or more appropriate final control elements.

Exemplary system 200 in additional embodiments includes other subsystems, including a nutrient and/or a mineral supply subsystem and a heat transfer unit operation(s). Exemplary system 200 stimulates production of biomass by introducing gaseous substrate(s) and nutrient(s) to a liquid culture medium to form a multi-phase mixture of the liquid culture medium, supplied gaseous substrate(s) and nutrient(s) within loop reactor 100. This multi-phase mixture flows through loop reactor 100 by the action of fluid flow unit operation 107. The liquid culture medium includes microorganisms capable of converting gaseous substrates to desirable products, some of which may be recovered from the microorganisms or from the gas phase and/or liquid phase that form in gas/liquid separation unit operation 109. Gaseous substrate(s) and nutrient(s) can be delivered to loop reactor 100 from nutrient supply subsystem, and loop reactor 100 is operated under conditions that promote mass transfer of gaseous substrate(s) and nutrient(s) into the liquid culture medium and into the microorganisms. Nutrients and minerals can be introduced into loop reactor 100 at one or more locations. Gas/liquid separation vessel 109 receives the liquid culture medium, including any gases that remain in the liquid culture medium, and gases which have separated from the liquid culture medium. Within gas/liquid separation vessel, the multi-phase liquid mixture separates into at least a liquid phase and a gas phase.

FIGS. 3-9 show an exemplary gas/liquid separation vessel 109 useful in a loop reactor 100 of system 200 for stimulating production of biomass. Exemplary system 200 includes a loop reactor 100 including a gas/liquid separation unit operation 109 (e.g., a gas/liquid separation vessel) where gases separate from liquid of the multi-phase mixture of liquid culture media including microorganisms and gases flowing through loop reactor 100. Elements of loop reactor 100 including but not limited to gas/liquid separation unit operation 109, e.g., a gas/liquid separation vessel 109, fluid flow unit operation 107 (e.g., pump or other device capable of causing a fluid to move), substantially horizontal zone 104, substantially vertical downflow zone 103 and substantially vertical upflow zone 105 can be a metallic, non-metallic, or composite structure. For example, the elements can include one or more metallic materials such as 304, 304L, 316, or 316L stainless steels. In some instances, one or more coatings, layers, overlays, inserts, or other materials can be deposited on, applied to, joined with, or formed integral to all or a portion of the metallic, non-metallic or composite structures to beneficially or detrimentally affect the ability for microbiological organisms to attach thereto or to grow thereupon. For example, a coating inhibiting the growth or attachment of microbiological organisms may be deposited on or formed integral with the surfaces of the loop reactor 100 that are thermally conductively coupled to a heat transfer unit operation. In another example, a coating that inhibits the growth or attachment of biological organisms may be deposited on or formed integral with portions of loop reactor 100 where it is desired to achieve removal of accumulated biomass more easily.

In at least some instances, the construction of elements of loop reactor 100 can include features that facilitate sterilization of all or a portion of the process contact surfaces. Such sterilization can be accomplished for example using steam sterilization, ultraviolet sterilization, chemical sterilization, or combinations thereof. In at least some instances, one or more non-metallic materials or one or more non-metallic coatings may be used within all or a portion of the interior or exterior of some or all of the elements of loop reactor 100. The use of such non-metallic materials may advantageously provide, for example, sterilizable surfaces that are capable of supporting or promoting biological growth.

Within gas/liquid separation vessel 109 the multi-phase mixture separates into at least a gas effluent and a liquid effluent. In at least some instances, biosolids present in the multi-phase mixture may be separated into a solids-containing effluent within gas/liquid separation vessel 109. In at least some instances, at least a portion of the solids-containing effluent from the gas/liquid separation vessel 109 can be combined with the one or more liquids and the mixture returned to gas/liquid separation vessel 109, loop section 104, substantially vertical downflow zone 103 or substantially vertical upflow zone 105. In at least some instances, system 200 can include one or more gas/liquid separators 109 operating in parallel or series.

Figure 3:
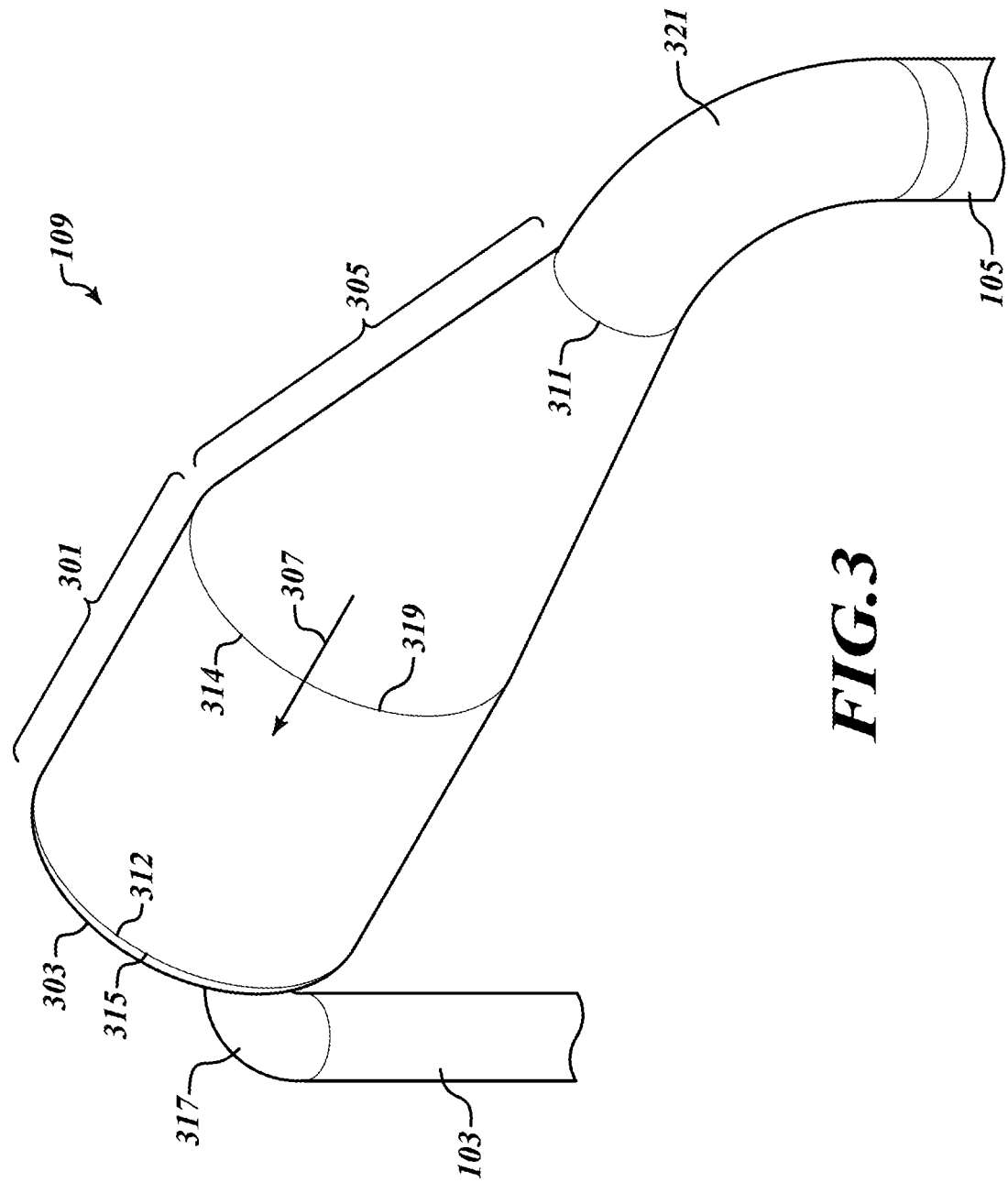
FIG. 3 shows a perspective view of an example of a gas/liquid separation vessel for use in a system for stimulating production of biomass according to one or more illustrated and described embodiments.
Figure 4:
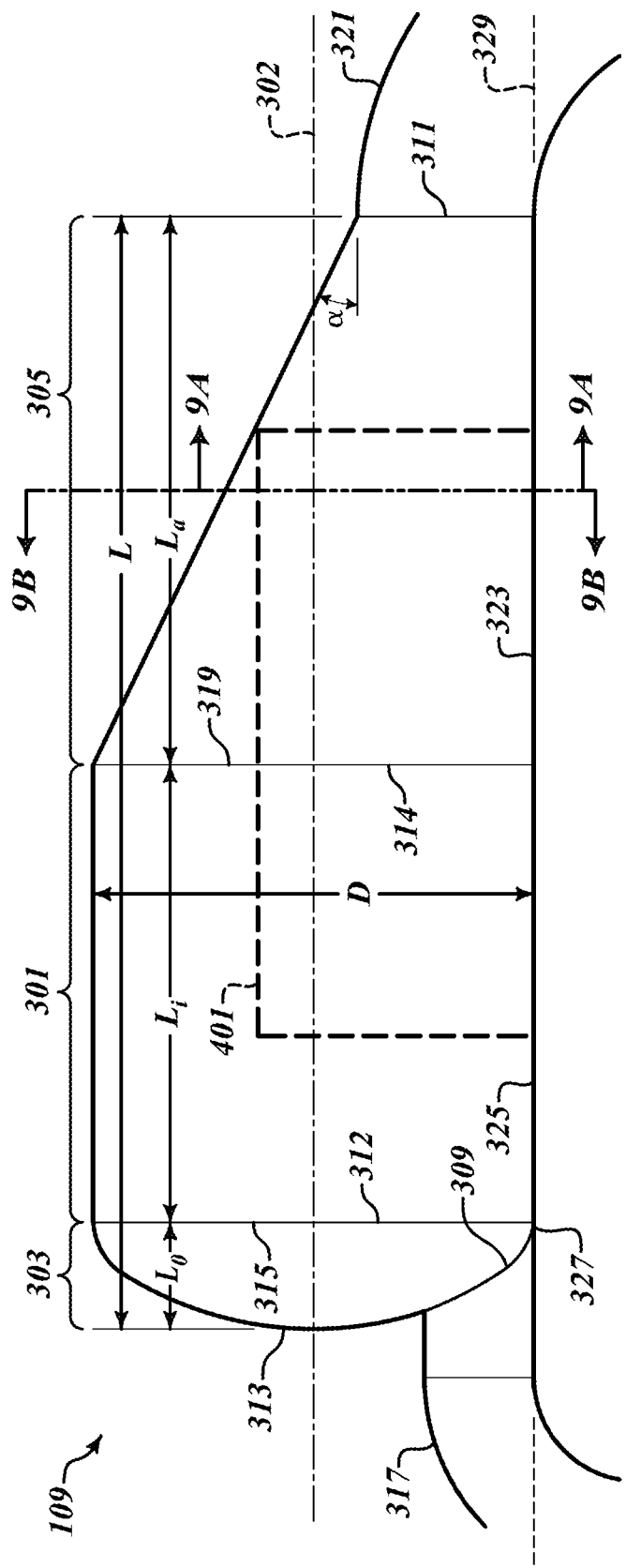
FIG. 4 shows an elevational view of a side of the gas/liquid separation vessel shown in FIG. 3.
Figure 5:
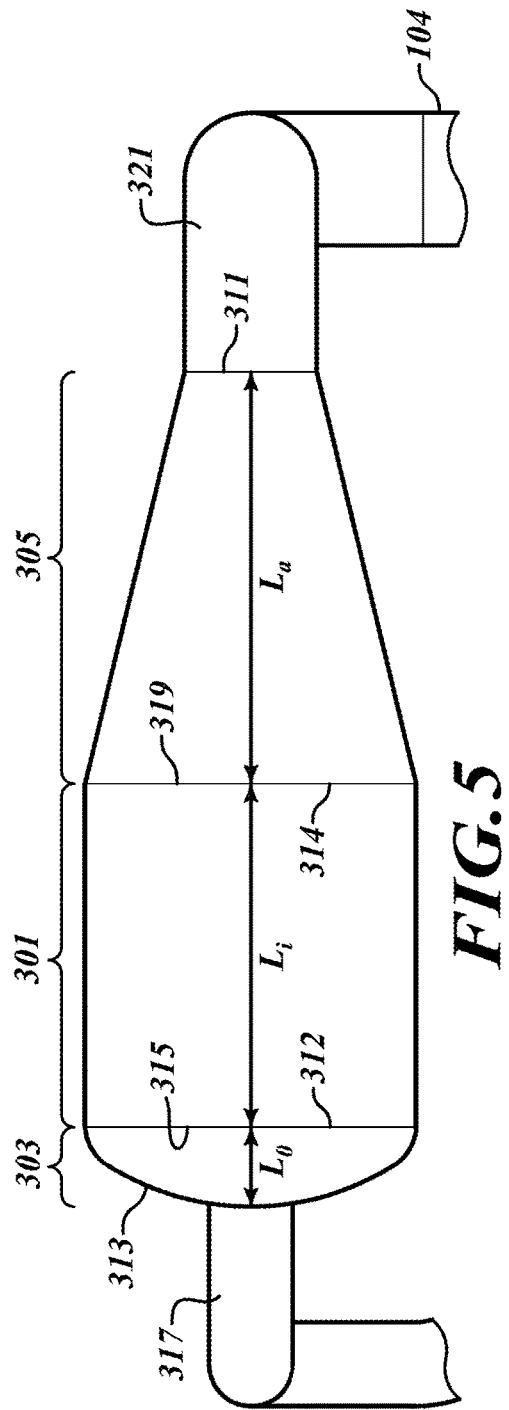
FIG. 5 shows a top view of the gas/liquid separation vessel shown in FIG. 3.
Figure 6:
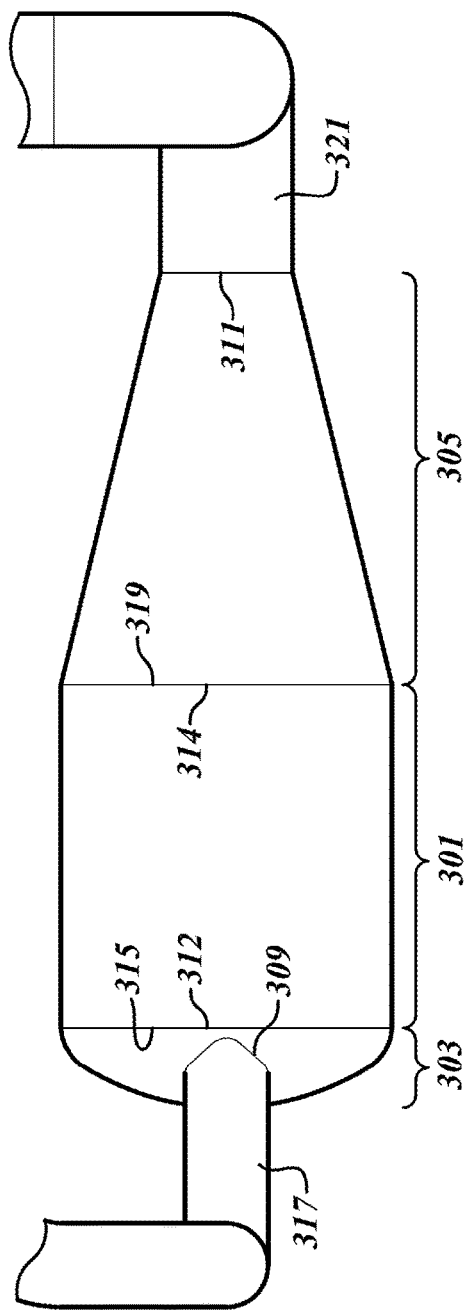
FIG. 6 shows a bottom view of the gas/liquid separation vessel shown in FIG. 3.
Figure 8:
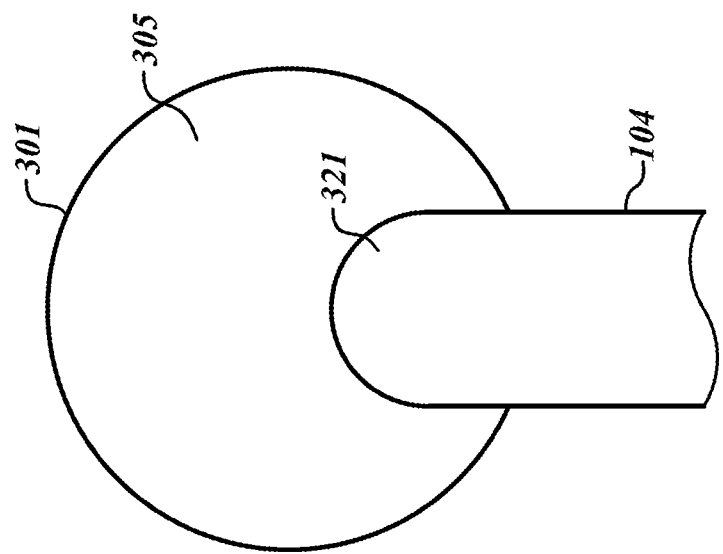
FIG. 8 shows an elevational view from the right or upstream end of the gas/liquid separation vessel shown in FIG. 3.
Figure 7:
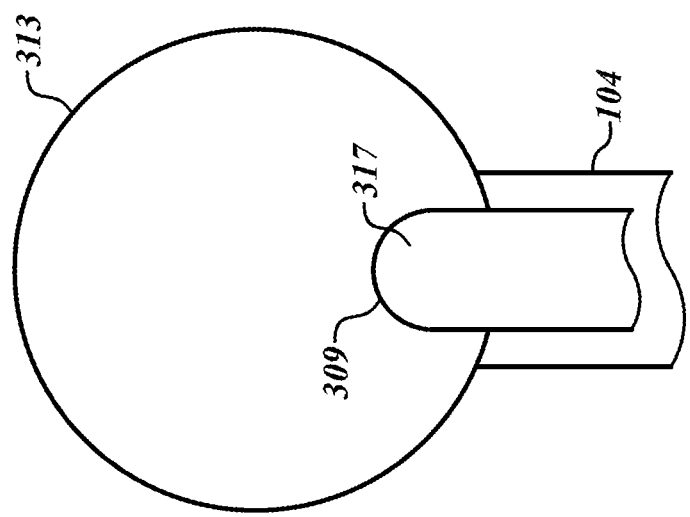
FIG. 7 shows an elevational view from the left or downstream end of the gas/liquid separation vessel shown in FIG. 3.
Figure 9B:
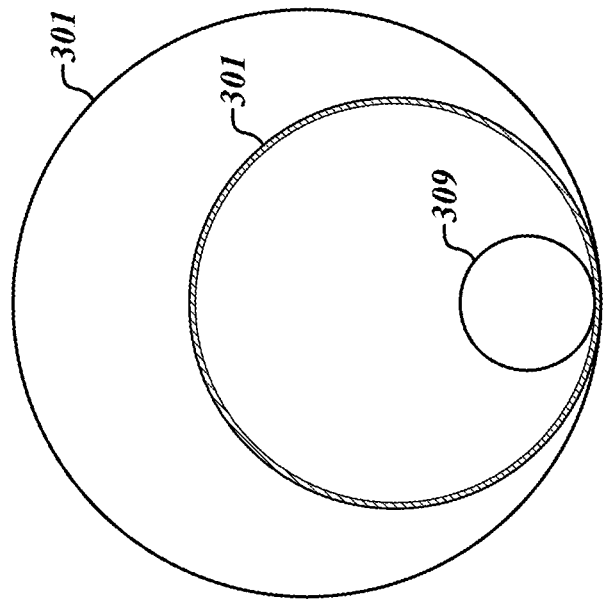
FIG. 9B shows a vertical cross-section through a gas/liquid separation vessel shown in FIG. 4 and taken along line 9B-9B in FIG. 4.
Figure 9A:
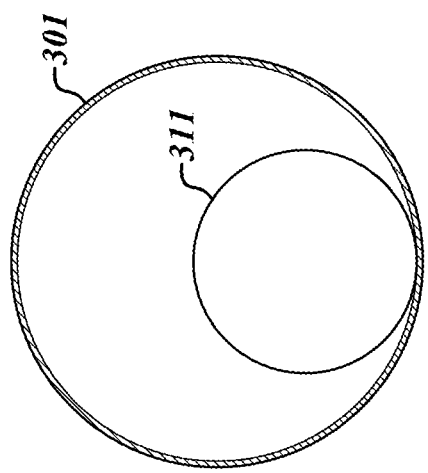
FIG. 9A shows a vertical cross-section through a gas/liquid separation vessel shown in FIG. 4 and taken along line 9A-9A in FIG. 4.

Referring to FIGS. 3 and 4, gas/liquid separation vessel 109 in accordance with embodiments described herein may be a longitudinal, horizontal vessel through which the multi-phase mixture flows in a horizontal direction. Gas/liquid separation vessel 109 includes an intermediate section 301, an outlet end section 303 and an inlet end section 305. Outlet end section 303 is located on the downstream side of intermediate section 301 while inlet end section 305 is located on the opposite side of intermediate section 301 upstream of intermediate section 301. In FIGS. 3 and 4, the multi-phase mixture flows through gas/liquid separation vessel 109 in the direction of arrow 307 in FIG. 3. Outlet end section 303 includes outlet 309 from gas/liquid separation vessel 109 and inlet end section 305 includes inlet 311 into gas/liquid separation vessel 109. Further details of intermediate section 301, outlet end section 303 and inlet end section 305 are described below.

In the illustrated embodiments shown in FIGS. 3-9, intermediate section 301 may be a non-rectangular, cylindrical member having a constant diameter D and a horizontal centerline defining a longitudinal axis 302 of gas/liquid separation vessel 109. An outlet 312 of intermediate section 301 is located at a downstream end of intermediate section 301 and an inlet 314 to intermediate section 301 is located at an upstream end of intermediate section 301. Diameter D can vary, with exemplary diameters D ranging from about 2 meters to about 8 meters and 3 meters to 6 meters; however, in other embodiments, diameter D may be less than 2 meters or more than 8 meters or less than 3 meters or more than 6 meters. Inlet 314 of intermediate section 301 and outlet 312 of intermediate section 301 are spaced apart by a length $L_i$. $L_i$ can vary, with exemplary values for $L_i$ ranging from about 2 meters to about 8 meters and 3 meters to 7 meters; however, in other embodiments, $L_i$ may be less than 2 meters or more than 8 meters and less than 3 meters or more than 7 meters. In the illustrated embodiment shown in FIGS. 3-9, intermediate section 301 is illustrated as being round in shape; however, intermediate section 301 is not limited to a round shape. For example, intermediate section 301 can have other non-rectangular shapes in a vertical cross-section.

Continuing to refer to FIGS. 3-9, outlet side section 303 includes a dished end 313 at the downstream end of gas/liquid separation vessel 109. Outlet side section 303 opposite dished end 313 includes an inlet end 315, which coincides with and is in fluid communication with outlet 312 of intermediate section 301. In the embodiment illustrated in FIGS. 3-9, inlet 315 of outlet side section 303 has a diameter that is equal to diameter D of intermediate section 301. While an embodiment of gas/liquid separation vessel 109 has been illustrated in FIGS. 3-9 with a dished end, gas/liquid separation vessel 109 is not limited to an outlet side section 303 that includes a dished end 313. In accordance with other embodiments of gas/liquid separation vessel 109, outlet side section 303 does not include a dished end 313. For example, the end of outlet side section 303 may have a shape that is not dished, for example, the end of the outlet side section 303 may not be dished and may be non-conical, e.g., flat or planar or other shape. Outlet side section 303 in the embodiment illustrated in FIGS. 3-9 has a length $L_o$ that is less than length $L_i$. $L_o$ can vary, for example, $L_o$ may range from about 0.5 meters to about 3 meters; however, in other embodiments, $L_o$ may be less than 0.5 meters or greater than about 3 meters. Dished end 313 includes an outlet or drain 309 in fluid communication with an inlet of substantially vertical downflow zone 103. Outlet 309 is located in a lower half or lower portion of dished end 313. Outlet 309 is connected to an inlet of substantially vertical down flow zone 103 by a 90° bend or drain conduit 317. Bend 317 has a radius which can vary, with exemplary radiuses ranging from about 0.5 to 3 times the diameter of the substantially vertical downflow zone 103; however, the radius of bend 317 can be less than 0.5 or more than 3 times the diameter of substantially vertical downflow zone 103. In accordance with embodiments described herein, outlet 309 of dished end 313 is in fluid communication with fluid moving device 107 via bend 317 and substantially vertical downflow zone 103 and the diameter of bend 317 and substantially vertical downflow zone 103 is non-increasing, i.e., diameter of bend 317 and substantially vertical downflow zone 103 is a constant or does not increase in diameter. In the illustrated embodiment, an inlet of bend or drain conduit 317 is in fluid communication with the outlet or drain 309 of dished end 313 and an outlet of bend or drain conduit 317 is in fluid communication with the inlet of vertical downflow zone 103.

Inlet side section 305 has the shape of an oblique conical frustum. As used herein the phrase "conical frustum" refers to a frustum (i.e., portion of a cone that lies between two parallel planes, e.g., horizontal planes, cutting through the cone) wherein the truncated ends of the cone resulting from the two parallel planes cutting through the cone are non-rectangular, i.e., not rectangular. For example, in accordance with embodiments described herein, both the truncated ends of the cone resulting from the two parallel planes cutting through the cone are circular or both are non-rectangular in shape. In other examples of embodiments described herein, the truncated end of the cone which has the larger diameter resulting from one of the parallel planes cutting through the cone is circular. As used herein, "cone" refers to the three-dimensional geometric shape that tapers smoothly from a flat base (e.g., circular) to a point called the apex or vertex. "Oblique conical frustum" refers to a conical frustum where the centers of the truncated ends of the cone defined by the parallel planes that cut through different sections of the cone do not have their axis on the same perpendicular, but instead two edges of the truncated ends of the cone defined by the parallel planes that cut through different portions of the cone are connected by the same perpendicular. In FIG. 4, inlet side section 305 includes an inlet 311 at an upstream end of inlet side section 305 and an outlet 319 at a downstream end of inlet side section 305. Outlet 319 of inlet side section 305 coincides with and is of the same diameter D as inlet 314 of intermediate section 301. In the embodiment shown in FIG. 4, inlet side section having the shape of an oblique conical frustum is lying on the edge that is common to each of the truncated ends of the cone that forms the oblique conical frustum. Outlet 319 defines one truncated end of the cone defined by one of the parallel planes that cuts through the cone and inlet 311 defines the other truncated end of the cone defined by the other parallel plane that cuts through the cone so as to define a conical frustum. The center of the base of the cone (i.e., at outlet 319) and the center of the other end of the cone (i.e., at inlet 311) making up the oblique conical frustum shape of inlet side section 305 do not lie in the same perpendicular if inlet side section 305 were rotated 90° in a counterclockwise direction from the position illustrated in FIG. 4. Rotating inlet side section 305 90° in a counterclockwise direction from the position illustrated in FIG. 4 would result in inlet end section 305 resting on the base of the cone (i.e., outlet 319) with the inlet 311 spaced vertically from outlet 319. In such orientation, an edge of the base of the cone (i.e., at outlet 319) defined by one parallel plane that cuts through the cone lies in the same perpendicular as an edge of the top of the cone (i.e., at the inlet 311) defined by the other parallel plane that cuts through the cone so as to define an oblique conical frustum. In the context of the orientation of inlet side section 305 illustrated in FIG. 4, inlet 311 of inlet side section 305 includes a lowermost edge and outlet 319 of inlet end section 305 includes a lower most edge that lie on, i.e., contact a common horizontal plane 329. In the embodiment illustrated in FIG. 4, intermediate section 305 includes a lowermost edge 325 and outlet end section 303 includes a lowermost edge 327 that also lie on, i.e., contact common horizontal plane 329. The oblique conical frustum shape of inlet end section 305 may also be characterized by cone angle α which ranges between about 5 to 30°. While the cone angle α can range between 5 and 30°, in other embodiments, the cone angle α may be less than 5° or greater than 30°.

Inlet 311 of inlet side section 305 has a diameter that is less than the diameter of outlet 319. Inlet 311 is in fluid communication with an outlet of bend or feed conduit 321. An inlet of bend or feed conduit 321 is in fluid communication with an outlet of substantially vertical upflow zone 105. Bend 321 has a radius which can vary, with exemplary radiuses ranging from about 0.5 to 3 times the diameter of substantially vertical upflow zone 105; however, in other embodiments, the radius of bend 321 can be less than 0.5 or more than 3 times the diameter of substantially vertical upflow zone 105. Inlet 311 of inlet side section 305 is spaced from outlet 319 of inlet side section 305 by a distance $L_a$. $L_a$ can vary, for example, $L_a$ may range from about 2 meters to about 10 meters or 4 meters to 8 meters; however, in other embodiments, $L_a$ may be less than 2 meters or greater than about 10 meters or less than 4 meters or greater than 8 meters. The length L of gas/liquid separation vessel 109 is equal to the sum of lengths $L_i$, $L_o$ and $L_a$. A ratio of $L_o/L$ can range from about 0.08 to 0.2; however, in other embodiments, the ratio of $L_o/L$ can be less than 0.08 or greater than 0.2. A ratio of $L_i/L$ can range from about 0.3 to 0.5; however, in other embodiments, the ratio of $L_i/L$ can be less than 0.3 or greater than 0.5. A ratio of $L_a/L$ can range from about 0.4 to 0.6; however, in other embodiments, the ratio of $L_a/L$ can be less than 0.04 or greater than 0.6.

When a multi-phase mixture is flowing through gas/liquid separation vessel 109 a gas head space exists above the multi-phase mixture within gas/liquid separation vessel 109. Gas which desorbs from the multi-phase mixture can collect in this gas head space. Specific embodiments of gas/liquid separation vessels 109 in accordance with embodiments described herein are shaped and sized so that this gas head space is characterized by a ratio of hydraulic diameter ($D_h$) to length ($L_g$) where $D_h$ is the hydraulic diameter of the volume within gas/liquid separation vessel 109 occupied by the gas head space and $L_g$ is the length of the interface between the multi-phase mixture and gas head space within gas/liquid separation vessel 109. $D_h=4A/P$ where A is the gas-wetted cross-sectional area of gas/liquid separation vessel 109 and P is the gas-wetted perimeter of the gas-wetted cross-section of gas/liquid separation vessel 109. Ratios of $D_h$ to $L_g$ can vary depending on the size and shape of gas/liquid separation vessel 109 and the level of the multi-phase mixture within the gas/liquid separation vessel 109. For example, when the depth of the multi-phase mixture within gas/liquid separation vessel 109 ranges between 50 to 90 percent of the diameter of intermediate section 301 of gas/liquid separation vessel 109, the ratio of $D_h$ to $L_g$ is selected to be less than about 5 or less than 5. Liquid effluent and biosolids removed from gas/liquid separation vessel 109 may be received at inlet of fluid moving device 107, e.g., a pump, and output from an outlet of fluid moving device 107. Outlet of fluid moving device 107 is in fluid communication with inlet of loop section 104 of loop reactor 100. Suitable pumps for moving liquid effluent and biosolids include pumps capable of moving fluids (liquids or gases) and slurries, by mechanical action and which are able to produce desired flow rates in the substantial absence of shear forces detrimental to the biomass and/or cavitation. Avoiding cavitation is desirable because cavitation causes gaseous substrates and nutrients in the multi-phase mixture to come out of solution making them less accessible to the biomass. Examples of such type of pumps are centrifugal pumps, although pumps which are not centrifugal pumps may also be used. For example, positive displacement pumps, progressive cavity pumps, double diaphragm pumps, and the like can also be used. Devices other than pumps can also be used to move the multi-phase mixture, for example, propellers driven by a motor, such as the propellers and motors described in U.S. Pat. No. 7,579,163 can be used instead of or in combination with a pump.

In exemplary embodiments described herein, gas pressure in headspace of gas/liquid separation unit operation 109 ranges from about 0.2 to about 0.6 bars; however, gas pressure in the headspace is not limited to a range of about 0.2 to about 0.6 bars. For example, in exemplary embodiments described herein, gas pressure in headspace can be less than 0.2 bars or greater than about 0.6 bars. The pressure at the inlet of fluid moving device 107 ranges from about 0.2 bars to about 4.0 bars; however, the pressure at the inlet of fluid moving device 107 is not limited to a range of about 0.2 bars to about 4.0 bars. For example, in exemplary embodiments described herein, the pressure at the inlet of fluid moving device 107 can be less than about 0.2 bars or greater than about 4.0 bars. The pressure at outlet of fluid moving device 107 ranges from about 3.5 bars to about 4.0 bars; however, the pressure at the outlet of fluid moving device 107 is not limited to a range of about 3.5 bars to about 4.0 bars. For example, in exemplary embodiments described herein, the pressure at the outlet of fluid moving device 107 can be less than about 3.5 bars or greater than about 4.0 bars. In exemplary embodiments that include static mixers in loop reactor 100, the pressure drop across a static mixer ranges from about 0.03 to about 0.05 bars; however, the pressure drop across a static mixer is not limited to a range from about 0.03 to about 0.05 bars. For example, in exemplary embodiments described herein, the pressure drop across a static mixer may be less than 0.03 bars or greater than 0.05 bars. In accordance with exemplary embodiments described herein, pressure within loop section 104 at the bottom or beginning of substantially vertical upflow zone 105 ranges from about 1.0 to about 3.0 bars; however, the pressure within loop section 104 at the beginning of substantially vertical upflow zone 105 is not limited to a range from about 1.0 to about 3.0 bars. For example, pressure within loop section 106 at the beginning of substantially vertical upflow zone 105 may be less than about 1.0 bars or greater than about 3.0 bars. In accordance with exemplary embodiments described herein, pressure at the outlet/top of substantially vertical upflow zone 105 ranges from about 0.2 bars to about 0.6 bars; however, the pressure at outlet/top of substantially vertical upflow zone 105 is not limited a range of about 0.2 bars to about 0.6 bars. For example, in accordance with embodiments described herein, pressure at outlet/top of substantially vertical upflow zone 105 can be less than about 0.2 bars or greater than about 0.6 bars. In embodiments described herein, the pressure drop across substantially vertical upflow zone 105 can range from about 1.0 bars to about 2.3 bars; however, the pressure drop across the substantially vertical upflow zone 105 is not limited to a range from about 1.0 bars to about 2.3 bars. For example, the pressure drop across the substantially vertical upflow zone 105 can be less than 1.0 bars or more than 2.3 bars. In some instances, the pressure drop across substantially vertical upflow zone 105 accounts for at least 20%, at least 30%, at least 40%, at least 50%, at least 60%, at least 70% or at least 80% of the pressure drop between the outlet of fluid moving device 107 and the headspace of gas/liquid separation vessel 109.

In at least some instances, gas effluent or the gas phase separated from the multi-phase mixture in gas/liquid separation vessel 109 may include a mixture of one or more gas substrates (e.g., methane or carbon monoxide) and one or more gaseous byproducts (e.g., carbon dioxide) generated as a byproduct by the biological organisms in loop reactor 100. In at least some instances, gas effluent may be separated from the multi-phased mixture in gas/liquid separation vessel 109 and at least a portion of the one or more gas substrates recycled (not shown) to the loop reactor 100, for example as a gas substrate. In at least some instances, the gas effluent may include one or more useful compounds. For example, the gas effluent may contain an amount of one or more gaseous $C_{2+}$ hydrocarbon compounds and compounds based thereupon having value as either a finished product or as a raw material in a subsequent process. Such useful compounds may be separated from the gas effluent prior to recycling at least a portion of the gas effluent to loop reactor 100.

In at least some instances, liquid effluent or the liquid phase separated from the multi-phased mixture in gas/liquid separation vessel 109 may include a mixture containing one or more liquids, nutrients, and the like introduced to the loop reactor 100 by a nutrient and/or mineral supply subsystem. In at least some instances, the liquid effluent may be removed from the loop reactor and returned to the gas/liquid separation vessel 109 by spraying onto the surface of the multi-phase mixture in the gas/liquid separation vessel 109 in order to reduce foaming within gas/liquid separation vessel 109. Anti-foam agents may be added to the liquid effluent sprayed into gas/liquid separation vessel 109 or maybe sprayed into gas/liquid separation vessel 109 without the liquid effluent. In at least some instances, the liquid effluent may include one or more useful compounds. For example, the liquid effluent may contain an amount of one or more liquid $C_{2+}$ hydrocarbon compounds including, but not, limited to alcohols, ketones, glycols, and other compounds based thereupon having value as either a finished product or as a raw material in a subsequent process. Such useful hydrocarbon compounds may be separated from the liquid effluent.

In some instances, systems for stimulating the production of biomass in accordance with embodiments described herein are used to produce natural or non-natural products, such as ethanol, acetate, butanol, isoprene, propylene, isoprene, enzymes, or other metabolites or cellular products wherein the product is derived from a microorganism. In such cases, the products may be present in either the gas phase or liquid phase separated in gas/liquid separation vessel 109 depending on the physical properties of the product.

As illustrated in FIG. 1, the outlet of fluid moving device 107 is in fluid communication with an inlet of substantially horizontal zone 104 of loop reactor 100. Substantially horizontal zone 104 of loop reactor 100 extends from its inlet to its outlet. The outlet of horizontal zone 104 is in fluid communication with the inlet to substantially vertical upflow zone 105. Substantially horizontal zone 104 can be formed from piping made from materials that do not adversely affect reaction/fermentation processes carried out using loop reactor 100. For example, substantially horizontal zone 104 can be formed from piping made from the materials described above for elements of loop reactor 100. The cross-sectional area of substantially horizontal zone 104 may be constant or substantially horizontal zone 104 may include one or more sections that have different cross-sectional areas. Reference to the cross-sectional area of substantially horizontal zone 104 in the present disclosure does not include the cross-sectional area of gas/liquid separation vessel 109. The inner diameter of substantially horizontal zone 104 may vary, with exemplary diameters ranging from about 20 centimeters to 3 meters. Other exemplary diameters range from 25 centimeters to 2.5 meters. When substantially horizontal zone 104 includes sections of differing cross-sectional areas, the sections of substantially horizontal zone 104 having larger cross-sectional area have cross-sectional areas that are at most three times the cross-sectional area of the sections of substantially horizontal zone 104 having smaller cross-sectional areas. In other exemplary embodiments, sections of substantially horizontal zone 104 having larger cross-sectional area, have cross-sectional areas that are at most two times the cross-sectional area of the sections of substantially horizontal zone 104 having smaller cross-sectional areas. In yet other exemplary embodiments, sections of substantially horizontal zone 104 having larger cross-sectional area, have cross-sectional areas that are at most 0.5 times the cross-sectional area of sections of substantially horizontal zone 104 having smaller cross-sectional areas. The length of substantially horizontal zone 104 can vary depending upon a number of factors, including the desired length of time the multi-phase mixture resides in substantially horizontal zone 104. The length of substantially horizontal zone 104 may also be determined based on other factors such as, but not limited to total reactor/liquid volume desired, total pressure drop across substantially horizontal zone 104, desired substrate utilization and yield. In exemplary embodiments, substantially horizontal zone 104 can vary in the length at its centerline from about 30 m to about 250 m, 40 m to about 200 m, 50 m to about 150 m and 60 to about 100 m.

The embodiment of substantially horizontal zone 104 illustrated in FIG. 1 is U-shaped, including two elbows 137 that bend at 90° angles when viewed from above. Substantially horizontal zone 104 can take other shapes. For example, substantially horizontal zone 104 can include more than the two 90° elbows 137 or it can include more than one elbow that is less than 90°. In other embodiments, substantially horizontal zone 104 can include numerous elbows that are greater than 90° or less than 90°.

Outlet of substantially horizontal zone 104 may be elevated relative to the inlet of substantially horizontal zone 104. Substantially horizontal zone 104 may accommodate for this difference in elevation between its inlet and its outlet by being sloped. The specific slope of substantially horizontal zone 104 or portions of substantially horizontal zone 104 depend in part on the length of substantially horizontal zone 104, the vertical distance between the centerline of substantially horizontal zone 104 at its inlet and the centerline of substantially horizontal zone 104 at its outlet. Substantially horizontal zone 104 can be sloped upward from its inlet to its outlet to accommodate for the change in elevation between its inlet and its outlet. Alternatively, a portion of substantially horizontal zone 104 can be sloped downward and a portion of substantially horizontal zone 104 can be sloped upward. In such alternative embodiments, the portion of substantially horizontal zone 104 that is sloped upward accounts for the loss in elevation resulting from the presence of the downward sloped portion of substantially horizontal zone 104 and the difference in elevation between the inlet of substantially horizontal zone 104 and the outlet of substantially horizontal zone 104. For example, the portion of substantially horizontal zone 104 extending from its inlet to the first 90° elbow 137 in FIG. 1 can be sloped downward, and the portion of substantially horizontal zone 104 extending from the first or second elbow 137 can be sloped upward to the outlet of substantially horizontal zone 104.

Exemplary embodiments illustrated in FIG. 1 include a plurality of static mixers, positioned along the length of substantially horizontal zone 104. Benefits of the use of static mixers are described in U.S. Pat. No. 7,579,163 and include mixing of the nutrient gases into the multi-phase mixture. Exemplary types of static mixers are also described in the '163 patent. Static mixers that can be used in embodiments described are not limited to those described in the '163 patent. Static mixers other than those described in the '163 patent can be used in the embodiments described herein. For example, other types of static mixers are available from companies such as StaMixCo LLC of Brooklyn, N.Y. and Sulzer Management Ltd. of Winterthur, Switzerland.

In exemplary embodiments, system 200 includes a nutrient and/or mineral supply subsystem for introducing nutrients and minerals into substantially horizontal zone 104 at one or more locations. Such nutrients include nutrients capable of supporting or transporting dissolved or suspended sustenance to biomass forming microbiological organisms in the multi-phase mixture within the loop reactor 100. In exemplary embodiments, nutrients and minerals may be introduced at one or more locations along substantially horizontal zone 104. The nutrient supply subsystem may also provide gaseous substrates/nutrients for introduction into a liquid culture medium to form a multi-phase mixture of the liquid culture medium and supplied gaseous substrates/nutrients. Such gaseous substrates/nutrients can include a single gas or a combination of gases capable of supporting or providing sustenance or nutrients to the biomass producing biological organisms in the loop reactor 100. Exemplary nutrients include natural gas, nitrogen, oxygen and ammonia water. A source of steam can be provided for thermal energy and cleaning purposes. Nutrients that can be supplied by nutrient subsystem are not limited to natural gas, nitrogen, oxygen and ammonium water. Other nutrients/minerals, such as methane, syngas, water, phosphate (e.g., as phosphoric acid), nitrates, urea, magnesium, calcium, potassium, iron, copper, zinc, manganese, nickel, cobalt and molybdenum, typically used as sulfates, chlorides or nitrates can also be provided by the nutrient subsystem.

In exemplary embodiments, system 100 may include a heat transfer unit operation for introducing or removing thermal energy from the multi-phase mixture in loop reactor 100. The heat transfer unit operation can introduce thermal energy to or remove thermal energy from the multi-phase mixture in loop reactor 100 at one or more locations. In at least some instances, the microbiological activity that occurs within the loop reactor 100 generates heat as a byproduct. Left uncontrolled, such heat can adversely affect the metabolism or health of the microbiological organisms within the loop reactor 100. Alternatively, microbiological organisms may also have a temperature below which the metabolism or health of the organism is adversely affected. As such, the biological organisms within the loop reactor 100 have a defined temperature range providing optimal growth and metabolic conditions. In at least some instances, the multi-phase mixture within the loop reactor 100 can be maintained at a temperature of about 130° F. or less; about 120° F. or less; about 110° F. or less; about 100° F. or less; about 95° F. or less; about 90° F. or less; about 85° F. or less; or about 80° F. or less using the heat transfer unit operation. In at least some instances, the multi-phase mixture within the loop reactor 100 can be maintained at a temperature of from about 55° F. to about 120° F.; about 60° F. to about 110° F.; about 110° F. to about 120° F.; about 100° F. to about 120° F.; about 65° F. to about 100° F.; about 65° F. to about 95° F.; or about 70° F. to about 90° F. using heat transfer unit operation.

Gas/liquid separation vessel 109, substantially vertical upflow zone 105 and/or substantially horizontal zone 104 of loop reactor 100 may include a desorption gas inlet. Desorption gas inlet is in fluid communication with a source of desorption gas, e.g., nitrogen, and in fluid communication with gas/liquid separation vessel 109, substantially vertical upflow zone 105 and/or substantially horizontal zone 104 of loop reactor 100. Thus, in accordance with embodiments of loop reactors in accordance with embodiments described herein, desorption gas can be introduced into gas/liquid separation vessel 109, substantially vertical upflow zone 105 and/or substantially horizontal zone 104 of loop reactor 100. Introducing a desorption gas into the multi-phase mixture causes a decrease in the partial pressure of other gases present in the multi-phase mixture (e.g., carbon dioxide and methane). Reducing the partial pressure of other gases present in the multi-phase mixture can have the effect of reducing the mass transfer of nutrient gases into the microorganism and/or causing the other gases to come out of solution.

FIG. 10 shows a high level method of operation 500 of a system 200 for stimulating production of biomass using one or more loop reactors 100 described in detail above with regard to FIGS. 1-9. Such systems advantageously introduce one or more gaseous substrates and a liquid media containing one or more nutrients into a liquid culture media containing at least one microorganism capable of utilizing the gaseous substrates and liquid nutrients to grow. The combination of the one or more gaseous substrates, liquid media containing one or more nutrients and liquid culture media containing at least one microorganism results in a multi-phase mixture that is circulated through loop reactor 100. The conditions within loop reactor 100 promote mass transfer and subsequent microbiological uptake of the gaseous substrate and liquid nutrients, reduction of pressure within the loop reactor and desorption of gases from the multi-phase mixture. The multi-phase mixture after passing through the substantially horizontal zone 104 and the substantially vertical upflow zone 105 of loop reactor 100 is received by a gas/liquid separation unit operation 109 where the multi-phase mixture is separated into liquid and gas phases. The method commences at 502.

At 504 a gaseous substrate is dispersed within the liquid media to form the multi-phase mixture. Such dispersion may occur downstream of fluid moving device 107 and upstream of gas/liquid separation vessel 109. In some instances, gaseous substrate may be dispersed at multiple points along loop reactor 100 and the gaseous substrate at each dispersion point may have the same or a different temperature, pressure, composition, or combinations thereof. The ability to vary physical or compositional properties of the gaseous substrate at different locations along the loop reactor 100 advantageously permits the tailoring of the gaseous substrate not only to the specific microbiological species present in the multi-phase mixture, but also to the specific location of the microbiological species within loop reactor 100 based on the dispersion point of the gaseous substrate.

At 506 the multi-phase mixture is flowed through loop reactor 100. As the multi-phase mixture flows through the loop reactor 100, it may contact a plurality of static mixers located within loop reactor 100, which promote the mixing of the gaseous substrate and/or nutrients into the liquid culture medium. By adjusting or otherwise controlling the flow rate of the multi-phase mixture through loop reactor 100, the length of time the bubbles of gaseous substrate and nutrients are in contact with the microorganism(s) can be modified. Increasing the length of time the bubbles of gaseous substrate and nutrients are in contact with the microorganism(s) can increase the amount of mass transfer of gaseous materials into the microorganisms and the microbiological uptake of gaseous materials by the microorganism. Conversely, decreasing the length of time the bubbles of gaseous substrate and nutrients are in contact with the microorganism(s) can decrease the amount of mass transfer of gaseous materials into the microorganisms and the microbiological uptake of gaseous materials by the microorganisms. In some instances, the length of time the bubbles of the gaseous substrate and nutrients are in contact with the microorganisms can be measured and controlled. For example, control subsystem 290 in FIG. 2 can alter, adjust or control the fluid velocity of the multi-phase mixture through loop reactor 100. In some instances, the temperature, pressure, or composition of the gaseous substrate may be altered, adjusted or controlled via control subsystem 290 to maintain a desired gas substrate bubble size within loop reactor 100. In other instances, the temperature, pressure, or composition of the gas substrate may be altered, adjusted or controlled via control subsystem 290 to maintain the concentration of one or more gas substrate components (e.g., methane, carbon dioxide, hydrogen, oxygen, nitrogen, etc.) within the liquid phase of the multi-phase mixture.

At 508 the temperature of the multi-phase mixture within loop reactor 100 can be altered, adjusted, or controlled to maintain the temperature within a defined temperature range. In at least some instances, the defined temperature range may be selected or otherwise chosen based at least in part on the microbiological species used within system 100. Excess heat may be generated as a byproduct by the microbiological organisms responsible for at least a portion of the activity within system 200. This excess heat, if left uncontrolled, could inhibit or adversely affect the growth or metabolism of some or all of the microbiological organisms within system 200. In at least some instances, cooling of the multi-phase mixture in loop reactor 100 may be provided to maintain the temperature of the multi-phase mixture in loop reactor 100 within a defined range. Such cooling may include passage of a cooling media through reservoirs or coils thermally conductively coupled to the loop reactor 100 or a conduit which has diverted a portion of the multi-phase mixture out of the loop reactor 100 to a heat transfer unit operation. In at least some instances, control subsystem 290 may control the flow rate or temperature of the cooling media passed through the reservoirs or coils that are thermally conductively coupled to loop reactor 100 or a conduit which has diverted portion of the multi-phase mixture out of loop reactor 100 to a heat transfer unit operation. In other instances, the heat produced by the microbiological species may be insufficient to maintain the multi-phase mixture in loop reactor 100 within a desired temperature range. Such may occur, for example, in extremely cold environments where loop reactor 100 is located in an exposed or partially exposed exterior location. In some instances, the reservoirs or coils thermally conductively coupled to loop reactor 100 or the conduit which has diverted portion of the multi-phase mixture out of loop reactor 100 to a heat transfer unit operation may be used to warm the multi-phase mixture. In at least some instances, control subsystem 290 may control the flow rate or temperature of the warming media passed through the reservoirs or coils that are thermally conductively coupled to the loop reactor 100 or the conduit which has diverted portion of the multi-phase mixture out of the loop reactor 100 to a heat transfer unit operation.

At 510, the pressure on the gas substrate bubbles traveling with the multi-phase mixture through loop reactor 100 is decreased by flowing the multi-phase mixture through a substantially vertical upflow zone 105. The pressure decrease at 510 can, in some instances, advantageously increase the rate at which gas substrate bubbles and other gases desorb from the multi-phase mixture.

At 512, the multi-phase mixture exits substantially vertical upflow zone 105 and flows to the gas/liquid separation vessel 109. Gaseous material that has desorbed from the multi-phase mixture can also flow to the gas/liquid separation vessel 102 along with the multi-phase mixture. The multi-phase mixture entering the gas/liquid separation vessel 109 can include, but is not limited to the liquid containing unabsorbed nutrients, microorganisms and gas substrate bubbles containing undissolved and unabsorbed gas substrate. Gas and liquid entering gas/liquid separation vessel 109 separate into a gas phase and a liquid phase within gas/liquid separation vessel 109. Gases can be collected from the headspace of gas/liquid separation vessel 109 while liquid can be removed from the bottom of gas/liquid separation vessel 109. In addition to liquid, microorganisms can also be collected in gas/liquid separation vessel 109 and removed from the bottom thereof at step 514. The liquid and microorganisms removed from the bottom of gas/liquid separation vessel 109 can be delivered to the inlet of fluid moving device 107 via substantially vertical down flow zone 103 for recirculation through loop reactor 100. In at least some instances, at least a portion of the collected gas may be removed from gas/liquid separation vessel 109 and subsequently processed or separated. At least a portion of the collected gas may be recycled to the loop reactor as a gas substrate. In some instances, at least a portion of the collected gas may be sold or otherwise disposed of. In at least some instances, at least a portion of the collected gas may be sold or traded as a fungible commodity. In at least some instances, the collected gas may include one or more $C_{2+}$ hydrocarbon gases and compounds based thereupon having value as either a finished product or as a raw material in a subsequent process. In some instances, the reactor is used to produce natural or non-natural products, such as ethanol, acetate, butanol, isoprene, propylene, farnesene, enzymes, or other metabolites or cellular products wherein the product is derived from a microorganism. In such cases, the products may be present in either the gas effluent or the liquid effluent depending on the physical properties of the product.

In at least some instances, at least a portion of the collected liquid may be subsequently processed or separated. For example, at least a portion of the liquid separated from the multi-phase mixture, which may or may not include biosolids, can be recycled through loop reactor 100. For example, at least a portion of the separated liquid containing biosolids may be combined with additional liquids and flowed through the loop reactor 100. Such recycle may advantageously provide an ongoing, continuous or semi-continuous, inoculation of the loop reactor 100 with established biological species. In some instances, at least a portion of the separated liquid may be collected and sold or otherwise disposed of. In at least some instances, at least a portion of the separated liquid may be sold or traded as a fungible commodity. In at least some instances, the separated liquid may include one or more $C_{2+}$ hydrocarbon liquids, including but not limited to one or more alcohols, glycols, or ketones.

Figure 11:
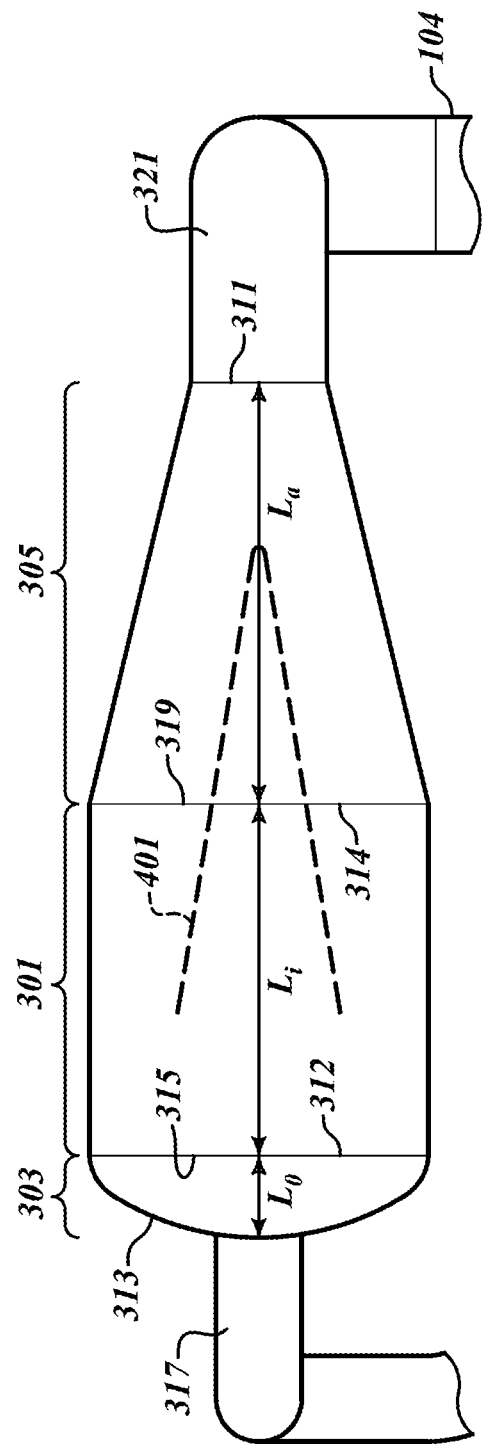
FIG. 11 shows a top view of another example of a gas/liquid separation vessel for use in a system for stimulating production of biomass according to one or more illustrated and described embodiments.

Referring to FIG. 11, in additional embodiments of the subject matter described herein, gas/liquid separation vessel 109 may include one or more flow guides 401 which cause flow of the multi-phase mixture within intermediate section 301 and inlet end section 305 of gas/liquid separation vessel 109 to occur with less channeling, less turbulence and/or less speed. Reducing channeling of the flow of the multi-phase mixture in intermediate section 301 and inlet end section 305, reducing turbulence of the flow of the multi-phase mixture in intermediate section 301 and inlet end section 305 and/or increasing residence time of the multi-phase mixture within intermediate section 301 and inlet end section 305 can result in an increase in the amount of gas that desorbs from the multi-phase mixture within gas/liquid separation vessel 109. One example of suitable flow guides 401 is illustrated in FIGS. 4 and 11 and includes a v-shaped vertical baffle 401 located within intermediate section 301 and inlet end section 305. Another example of a suitable flow guide includes two or more parallel vertical baffles located within intermediate section 301 and inlet end section 305. Such parallel vertical baffles have their lengths parallel with the direction of bulk flow of the multi-phase mixture through gas/liquid separation vessel 109.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other systems for stimulating the production of biomass, fermentors and fermentation systems. Such systems for stimulating the production of biomass, fermentors and fermentation systems may include loop reactors or fermentors for purposes other than chemical intermediate production, and may include loop reactors, fermentors and fermentation systems useful in food or beverage production. Similarly, the ancillary systems described herein, including the fluid moving device, nutrient and/or mineral supply subsystem, heat transfer unit operation and the control subsystem may include a single system, for example a package heat exchanger or package control system, or may include a custom designed subsystem including any number of sub-components that are physically, fluidly, and communicably coupled in a manner facilitating the controlled production and distribution of cooling or warming media (i.e., by the heat transfer unit operation). The control subsystem can include an integrated or distributed control system that provides monitoring, alarming, control, and control output for all or a portion of the biomass production system or any of the ancillary subsystems. The control subsystem may also include any number of individual loop controllers and the like for control of one or more aspects of the biomass production system or any of the ancillary subsystems.

The foregoing detailed description has set forth various embodiments of the devices and/or processes via the use of process flow diagrams and example methods. Insofar as such block diagrams, schematics, and examples contain one or more functions and/or operations, it will be understood by those skilled in the art that each function and/or operation within such block diagrams, flowcharts, or examples can be implemented, individually and/or collectively, using wide range of off-the-shelf or customized components that are well known to those of skill in the chemical engineering arts. The microbiological species listed herein are intended to provide a sample of the potential microbiological species that can be supported in a system for promoting the production of biomass and loop reactors as described herein.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system for stimulating production of biomass comprising:
 a loop reactor, the loop reactor including:
  a fluid moving device having an inlet and an outlet, the inlet of the fluid moving device in fluid communication with an outlet of a substantially vertical downflow zone;
  a loop section including an outlet and an inlet, the inlet of the loop section in fluid communication with the outlet of the fluid moving device;
  a substantially vertical upflow zone including an outlet and an inlet, the inlet of the substantially vertical upflow zone in fluid communication with the outlet of the loop section; and
 a gas/liquid separation vessel having a longitudinal axis and including:
  an outlet and an inlet, the inlet of the gas/liquid separation vessel located in a lower portion of the gas/liquid separation vessel and in fluid communication with the outlet of the substantially vertical upflow zone, the outlet of the gas/liquid separation vessel in fluid communication with an inlet of the substantially vertical downflow zone;
  an intermediate section between the outlet and the inlet of the gas/liquid separation vessel, the intermediate section having a constant diameter equal to D;
  an outlet side section on one side of the intermediate section, the outlet side section including the outlet of the gas/liquid separation vessel; and
  an inlet side section on a side of the intermediate section opposite the outlet side section, the inlet side section including the inlet of the gas/liquid separation vessel, the inlet side section having a shape of an oblique conical frustum and having an increasing diameter in a direction of fluid flow through the inlet side section.

2. The system of claim 1, further comprising a drain conduit including in inlet end and an outlet end, the inlet end of the drain conduit connected to the outlet side section of the gas/liquid separation vessel and the outlet end of the drain conduit connected to the substantially vertical downflow zone.

3. The system of claim 1, wherein a lowermost edge of the inlet, the outlet, the intermediate section, the outlet side section and the inlet side section of the gas/liquid separation vessel contact a common plane.

4. The system of claim 1, further comprising a feed conduit including an inlet and an outlet, the inlet of the feed conduit connected to the substantially vertical upflow zone and the outlet end of the feed conduit connected to the inlet side section of the gas/liquid separation vessel.

5. The system of claim 1, wherein the inlet side section having a shape of an oblique conical frustum includes a cone angle that ranges between 5 to 30°.

6. The system of claim 1, wherein the outlet of the gas/liquid separation vessel has a diameter that is less than a diameter of the inlet of the gas/liquid separation vessel.

7. The system of claim 1, wherein the inlet side section has a length measured along the longitudinal axis of the gas/liquid separation vessel that is greater than a length of the intermediate section measured along the longitudinal axis of the gas/liquid separation vessel and greater than a length of the outlet side section measured along the longitudinal axis of the gas/liquid separation vessel.

8. The system of claim 1, wherein the outlet side section has a dished shape.

9. The system of claim 1, wherein the substantially vertical downflow zone has a diameter that is non-increasing.

10. The system of claim 2, wherein the drain conduit has a diameter that is non-increasing.

11. The system of claim 1, wherein D ranges from 2 meters to 8 meters.

12. A gas/liquid separation vessel comprising:
an outlet, an inlet, and a longitudinal axis, the inlet of the gas/liquid separation vessel located in a lower portion of the gas/liquid separation vessel;
an intermediate section between the outlet and the inlet of the gas/liquid separation vessel, the intermediate section having a constant diameter equal to D;
an outlet side section on one side of the intermediate section, the outlet side section including the outlet of the gas/liquid separation vessel; and
an inlet side section on a side of the intermediate section opposite the outlet side section, the inlet side section including the inlet of the gas/liquid separation vessel, the inlet side section having a shape of an oblique conical frustum and having an increasing diameter in a direction of fluid flow through the inlet side section.

13. The gas/liquid separation vessel of claim 12, wherein a lowermost edge of the inlet, the outlet, the intermediate section, the outlet side section and the inlet side section of the gas/liquid separation vessel contact a common plane.

14. The gas/liquid separation vessel of claim 12, wherein the inlet side section having a shape of an oblique conical frustum includes a cone angle that ranges between 5 to 30°.

15. The gas/liquid separation vessel of claim 12, wherein the outlet of the gas/liquid separation vessel has a diameter that is less than a diameter of the inlet of the gas/liquid separation vessel.

16. The gas/liquid separation vessel of claim 12, wherein the inlet side section has a length measured along the longitudinal axis of the gas/liquid separation vessel that is greater than a length of the intermediate section measured along the longitudinal axis of the gas/liquid separation vessel and greater than a length of the outlet side section measured along the longitudinal axis of the gas/liquid separation vessel.

17. The gas/liquid separation vessel of claim 12, wherein the outlet side section has a dished shape.

18. The gas/liquid separation vessel of claim 12, wherein D ranges from 2 meters to 8 meters.

19. The gas/liquid separation vessel of claim 12 wherein the intermediate section includes an inlet and an outlet, the inlet of the intermediate section and the outlet of the intermediate section spaced apart by a length L ranging from 2 meters to 8 meters.

20. The gas/liquid separation vessel of claim 12, wherein the inlet side section having a shape of an oblique conical frustum includes a cone angle that is less than 5°.

21. The gas/liquid separation vessel of claim 12, wherein the inlet side section having a shape of an oblique conical frustum includes a cone angle that is greater than 30°.

* * * * *